US00RE39744E

(19) United States
(12) Reissued Patent
Ishii et al.

(10) Patent Number: US RE39,744 E
(45) Date of Reissued Patent: Jul. 24, 2007

(54) ADAMANTANE DERIVATIVES AND PROCESS FOR PRODUCING THEM

(75) Inventors: Yasutaka Ishii, Takatsuki (JP); Tatsuya Nakano, Himeji (JP); Naruhisa Hirai, Himeji (JP)

(73) Assignee: Daicel Chemical Industries, Ltd., Osaka (JP)

(21) Appl. No.: 10/830,494

(22) PCT Filed: Mar. 5, 1998

(86) PCT No.: PCT/JP98/00904

§ 371 (c)(1),
(2), (4) Date: Nov. 10, 1998

(87) PCT Pub. No.: WO98/40337

PCT Pub. Date: Sep. 17, 1998

Related U.S. Patent Documents

Reissue of:
(64) Patent No.: 6,392,104
Issued: May 21, 2002
Appl. No.: 09/180,478
Filed: Nov. 10, 1998

(30) Foreign Application Priority Data

Mar. 11, 1997 (JP) ..... 9-056516
Aug. 4, 1997 (JP) ..... 9-209431

(51) Int. Cl.

| | |
|---|---|
| ***C07C 35/22*** | (2006.01) |
| ***C07C 61/12*** | (2006.01) |
| ***C07C 211/00*** | (2006.01) |
| ***C07D 207/40*** | (2006.01) |
| ***C07D 207/444*** | (2006.01) |
| ***C07D 204/24*** | (2006.01) |
| | B01J 31/00 |

(52) U.S. Cl. ..... 568/818; 548/545; 548/549; 548/551; 548/552; 548/152; 562/499; 562/502; 562/501; 564/457; 564/458; 502/167

(58) Field of Classification Search ..... 562/498, 562/499, 501.502; 548/152, 545, 549, 551, 548/552; 564/457, 458; 568/818; 502/167
See application file for complete search history.

(56) References Cited

U.S. PATENT DOCUMENTS

| | | | |
|---|---|---|---|
| 3,356,741 | A | 12/1967 | Schneider |
| 3,450,775 | A | 6/1969 | Schneider |
| 3,594,427 | A | 7/1971 | Moore |
| 3,753,950 | A | 8/1973 | Thompson |
| 3,760,020 | A | 9/1973 | Moore |

(Continued)

FOREIGN PATENT DOCUMENTS

| | | |
|---|---|---|
| JP | 4216621 | 9/1942 |
| JP | 4226792 | 12/1942 |
| JP | 43-937 B | 1/1968 |
| JP | 4412891 | 6/1969 |
| JP | 4628419 | 8/1971 |
| JP | 5021090 | 3/1975 |
| JP | 63307844 | 12/1988 |
| JP | 2196744 | 8/1990 |
| JP | 838909 | 2/1996 |
| WO | WO9640641 | 12/1996 |

OTHER PUBLICATIONS

Kontani et al, A New combined Oxidizing Reagent System, Nov. 1985, Chem. & Pharm. Bulletin, 33 (11), p. 4680–4684.*
G.R. Newkome et al., J. Org. Chem, vol. 57, No. 1, 1992, pp. 358–362.
A. Bashir–Hashemi et al., Tetrahedron Letters, vol. 36, No. 8, 1995, pp. 1233–1236.
R.E. Moore et al., J. Org. Chem., vol. 43, No. 26, 1978, pp. 4978–4980.
I.N. Butenko et al., Synthetic Communications, vol. 14, No. 2, 1984, pp. 113–119.
S. Grimme et al., Chem. Ber, 127, (1994), pp. 2081–2088.
Dolgopolpva, T.N., et al. "Thin–layer chromatography of oxygen–containing derivatives of adamantane" Zh. Anal. Khim., (1989),44(9), p. 1689–1690.
Tadashi Sasaki et al., "Synthesis of adamantane derivatives" J. Org. Chem., (1982), 47, p. 3219–3224.
Kozlovskii, Ya. B. et al., (1989), 25(6), p. 1222–1226.
Vishnevskii, E.N. et al. (1996), 32(7), p. 1030–1035.
Kontani, et al., A New Combined Oxidizing Reagent System, Nov. 1985, Chem. & Pharm. Bulletin, 33(11), p. 4680–4684.

*Primary Examiner*—Thomas McKenzie
*Assistant Examiner*—Taylor Victor Oh
(74) *Attorney, Agent, or Firm*—Birch, Stewart, Kolasch & Birch, LLP

(57) ABSTRACT

In the presence of an imide compound (e.g., N-hydroxyphthalimide) shown by the formula (2):

(2)

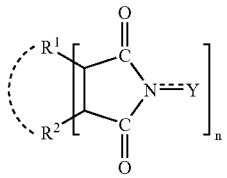

wherein $R^1$ and $R^2$ independently represents a hydrogen atom, a halogen atom, an alkyl group, an aryl group, a cycloalkyl group; or $R^1$ and $R^2$ may bond together to form a double bond or an aromatic or non-aromatic ring; Y is O or OH and n=1 to 3;

or the imide compound and a co-catalyst (e.g., a transition metal compound), an adamantane derivative having a functional group such as a nitro group, an amino group, a hydroxyl group, a carboxyl group, a hydroxymethyl group and an isocyanato group is oxidized with oxygen. According to the above method, an adamantane derivative having a hydroxyl group together with a functional group such as a nitro group, an amino group, a hydroxyl group, a carboxyl group, a hydroxymethyl group and an isocyanato group is efficiently obtained.

13 Claims, No Drawings

U.S. PATENT DOCUMENTS

| | | | |
|---|---|---|---|
| 3,832,332 | A | 8/1974 | Thompson |
| 3,994,960 | A | 11/1976 | Yamazaki et al. |
| 4,476,060 | A | 10/1984 | Gilbert |
| 5,030,739 | A | 7/1991 | Foricher et al. |
| 5,958,821 | A | 9/1999 | Ishii et al. |
| 6,207,342 | B1 | 3/2001 | Takechi et al. |
| 6,235,851 | B1 | 5/2001 | Ishii et al. |
| 6,468,487 | B1 | 10/2002 | Ishii et al. |

* cited by examiner

ADAMANTANE DERIVATIVES AND PROCESS FOR PRODUCING THEM

Matter enclosed in heavy brackets [ ] appears in the original patent but forms no part of this reissue specification; matter printed in italics indicates the additions made by reissue.

This application is the national phase under 35 U.S.C. §371 or prior PCT International Application No. PCT/JP98/00904 which has an International filing date of Mar. 5, 1998 which designated the United States of America, the entire contents of which are hereby incorporated by reference.

TECHNICAL FIELD

This invention relates to a novel adamantane derivative, which has a hydroxyl group together with a nitro group, an amino group, an acyloxy group, a carboxyl group, a hydroxymethyl group or the like, and to a process for producing the same.

BACKGROUND ART

The adamantane has a three-dimensionally symmetric structure and skeletons which insure mutual stabilization of each ring, and, as a result, endowed with distinctive functions. Various copolymers each having enhanced or improved functions or characteristics can be obtained by introducing a hydroxyl group into an adamantane and, if necessary, inducing them into an acrylic acid derivative or a carbonate. There have been proposed various production processes for obtaining such copolymers from a functional group (e.g., a hydroxyl group, an amino group, a carboxyl group)-introduced adamantane. The processes include, for example, a process of producing a polyester [e.g., Japanese Patent Application Laid-open No. 21090/1975 (JP-A-50-21090)], a process of producing a polycarbonate [e.g., U.S. Pat. No. 3,594,427], a process for producing a polyamide or a polyimide [e.g., U.S. Pat. No. 3,832,,332], a process for producing a polyurethane [e.g., Japanese Patent Publication No. 12891/1969 (JP-B-44-12891)], a process for producing a polysulfone and a polysulfonate [e.g., U.S. Pat. No. 3,753,950], and a process for producing a vinyl polymer [e.g., Japanese Patent Publication No. 28419/1971 (JP-B-46-28419)].

Generally, these polymers provided from an adamantane derivative have excellent functions or characteristics (high functionality) such as, for example, small light-inducing loss, high refractive index, double refraction index and other optical characteristics, and moisture resistance, excellent heat resistance, coefficient of thermal expansion and other characteristics. Such excellent characteristics cannot be achieved by using conventional polymers. Accordingly, they have been investigated applications of said polymer for optical fibers, optical elements, optical lenses, hologram, optical discs, contact lenses and other optical materials, transparent resin coating compositions for organic glasses, electric conductive polymers, photosensitive materials, fluorescent materials and so forth.

Moreover, an amino derivative derived from an alcohol of an adamantane is useful for introducing various pharmaceuticals and/or agricultural chemicals each having excellent pharmacological activity, and is utilized for producing a therapeutic agent for Parkinson's disease such as "SYMMETREL" (a trade name).

Thus, an adamantane having a functional group such as a hydroxyl group is applied to various uses.

As a process for producing an alcohol of the adamantane, there have been proposed process, such as a process for hydrolyzing a bromide of adamantane [Japanese Patent Application Laid-open No. 196744/1990 (JP-A-2-196744)], a process for oxidizing an adamantane using chromic acid [Japanese Patent Publication No. 16621/1967 (JP-B-42-16621)], a process for oxidizing a fused adamantane with oxygen using a cobalt salt as a catalyst [Japanese Patent Publication No. 26792/1967 (JP-B-42-26792)], a biological process [J. Chem. Soc., Chem. Comm., 1833 (1996)]. However, introduction of a hydroxyl group (specifically, a plurality of hydroxyl groups) to adamantane by using these processes is difficult.

Japanese Patent Application Laid-open No. 38909/1996 (JP-A-8-38909) proposes a process for oxidizing a substrate with oxygen by using an imide compound as a catalyst. By applying the above oxidation process to the oxidation of a substrate such as adamantane, an adamantanol is obtained.

It is, therefore, an object of the present invention to provide a novel adamantane derivative and a process for producing the same.

It is another object of the present invention to provide an adamantane derivative having at least one hydroxyl group and at least one functional group selected from a nitro group, an amino group, an acylamino group, a carboxyl group, hydroxymethyl group and other groups, and a process for producing the same.

A further object of the invention is to provide a process for producing the above mentioned adamantane derivative effectively with high transformation rate or conversion and selectivity even under mild or moderate conditions.

DISCLOSURE OF INVENTION

The present inventors did intensive investigation to accomplish the above objects, and as a result, found that oxidation of a specific adamantane derivative with oxygen by using an oxidation catalyst comprising a specific imide compound or the imide compound and a co-catalyst provides a novel adamantane derivative efficiently.

Thus, a novel adamantane derivative of the present invention is shown by the following formula (1):

(1)

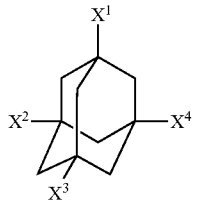

wherein $X^1$ represents a hydroxyl group which may be protected by a protective group, $X^2$ represents a nitro group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group;

(i) when $X^2$ is a nitro group, $X^3$ and $X^4$ may be the same or different from each other and each may represent a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protection group, or an isocyanato group, excluding the case where $X^3$ and $X^4$ are both hydrogen atoms when $X^1$ is hydroxyl group;

(ii) when $X^2$ is an amino group or N-substituted amino group which may be protected by a protective group, $X^3$ and $X^4$ may be the same or different from each other and each may represent a hydrogen atom, an alkyl group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group, excluding the case where $X^3$ and $X^4$ are both hydrogen atoms or alkyl groups when $X^1$ is hydroxyl group;

(iii) when $X^2$ is a hydroxyl group which may be protected by a protective group, $X^3$ and $X^4$ may be the same or different from each other and each may represent a hydrogen atom, an alkyl group, a hydroxyl group which may be protected by a protective group, a carboxyl group which may be protected by a protective group, a hydroxymethyl group which may be protected by a protective group, or an isocyanato group, excluding the case where $X^3$ and $X^4$ are both hydrogen atoms or alkyl groups when $X^1$ is hydroxyl group or a saturated aliphatic acyloxy group and $X^2$ is hydroxyl group or a saturated aliphatic acyloxy group and excluding the case where $X^3$ and $X^4$ is a combination of hydrogen atom and a carboxyl group which may be protected by a protective group when $X^1$ and $X^2$ are both hydroxyl groups;

(iv) when $X^2$ is a carboxyl group which may be protected by a protective group, $X^3$ and $X^4$ may be the same or different from each other and each may represent a hydrogen atom, an alkyl group, a carboxyl group which may be protected by a protective group, a hydroxymethyl group which may be protected by a protective group, or an isocyanato group, excluding the case where $X^3$ and $X^4$ are both hydrogen atoms or alkyl groups or a combination of a hydrogen atom and an alkyl group when $X^1$ is a hydroxyl group or a saturated aliphatic acyloxy group;

(v) when $X^2$ is a hydroxymethyl group which may be protected by a protective group, $X^3$ and $X^4$ may be the same or different from each other and each may represent a hydrogen atom, an alkyl group, a hydroxymethyl group which may be protected by a protective group, or an isocyanato group, excluding the case where, $X^3$ and $X^4$ are both hydrogen atoms when $X^1$ is hydroxyl group;

(vi) when $X^2$ is an isocyanato group, $X^3$ and $X^4$ may be the same or different from each other and each may represent a hydrogen atom, an alkyl group or an isocyanato group, excluding the case where, $X^3$ and $X^4$ are both hydrogen atoms when $X^1$ is hydroxyl group.

The adamantane derivative can be obtained, in the presence of an oxidation catalyst comprising an imide compound shown by the following formula (2):

(2)

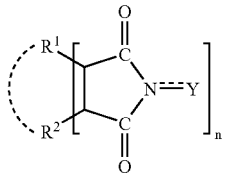

wherein $R^1$ and $R^2$ may be the same or different from each other and each may represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond or an aromatic or non-aromatic ring; Y represents an oxygen atom or a hydroxyl group; and n denotes an integer of 1 to 3; by contacting an adamantane derivative shown by the following formula (1a):

(1a)

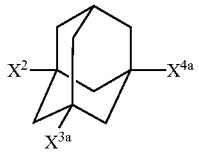

wherein $X^2$ represents a nitro group, an amino group or N-substituted amino group which may be protected by a protective group, a hydroxy group which may be protected by a protective group, a carboxyl group which may be protected by a protective group, a hydroxymethyl group which may be protected by a protective group, or an isocyanato group; $X^{3a}$ and $X^{4a}$ may be the same or different from each other and each may represent a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanato group; with oxygen.

The present invention also includes a process for producing an adamantane derivative having at least a hydroxyl group which comprises subjecting an adamantane derivative shown by the following formula (1a):

(1a)

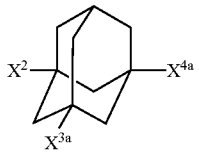

wherein $X^2$ represents a nitro group, a hydroxyl group which may be protected by a protective group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group; $X^{3a}$ and $X^{4a}$ may be the same or different from each other and each may represent a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanate group; to at least one step selected from the following oxidation step (i), nitration step (ii) and carboxylation step (iii):

(i) an oxidation step by oxygen in the presence of a catalyst comprising an imide compound shown by the formula (2)

(ii) at least one nitration step of the following (iia), (iib) and (iic):

(iia) a nitration step by a nitrogen oxide in the presence of a catalyst comprising an imide compound shown by the formula (2);

(iib) a nitration step by oxygen and at least one nitrogen oxide selected from dinitrogen oxide and nitrogen monoxide, and oxygen; and (iic) a nitration step by nitrogen dioxide (iii) a carboxylation step by carbon monoxide and oxygen in the presence of a catalyst comprising an imide compound shown by the formula (2).

The catalyst may comprise an imide compound shown by the formula (2) and a co-catalyst (e.g., a compound containing a transition metal element).

Incidentally, in the present specification, the term "protective group" is used in a wide sense and includes a group derived from a free functional group. The protective group incapable of being eliminated may be employed.

Further, the term "functional group" may be used as a general term, simply referring to a nitro group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group. An amino group or N-substituted amino group which may be protected by a protective group may be referred to simply as an amino group.

BEST MODE FOR CARRYING OUT THE INVENTION

[Adamantane Derivative]

In the adamantane derivative shown by the formula (1), as a protective group for hydroxyl gruop and hydroxymethyl group (a moiety corresponding to the hydroxyl group of the hydroxymethyl group) there may be mentioned, for instance, t-butyl group, a cycloalkyl group (e.g., cyclohexyl group), an aryl group (e.g., 2,4-dinitrophenyl group), an aralkyl group (e.g., benzyl group, 2,6-dichlorobenzyl group, 3-bromobenzyl group, 2-nitrobenzyl group, 4-dimethylcarbamoylbenzyl group, a benzyl group which may have a substituent such as triphenylmethyl group), tetrahydropyranyl group, a non-polymerizable acyl group [e.g., a saturated aliphatic acyl group (e.g., a saturated $C_{2-6}$aliphatic acyl group such as acetyl group, propionyl group, isopropionyl group, butyryl group, isobutyryl group, valeryl group, isovaleryl group, pyvaloyl group, prefferably a saturated $C_{2-4}$aliphatic acyl group), an aromatic acyl group (e.g., a $C_{7-13}$aromatic acyl group such as benzoyl group, p-phenylbenzoyl, phthaloyl, naphtoyl), an alicyclic acyl group (a cycloalkyl-carbonyl group: such as cyclohexylcarbonyl)], an alkoxycarbonyl group such as a $C_{1-6}$-alkoxy-carbonyl group (e.g., methoxycarbonyl group, ethoxycarbonyl group, propyloxycarbonyl group, isopropyloxycarbonyl group, isobutyloxycarbonyl group, t-butoxycarbonyl group), an alalkyloxycarbonyl group (e.g., benzyloxycarbonyl group, methoxybenzyloxycarbonyl group), a carbamoyl group which may have a substituent such as a $C_{1-6}$alkyl group, a $C_{6-14}$aryl group (e.g., carbamoyl group, methylcarbamoyl group, ethylcarbamoyl group, phenyl carbamoyl group), a dialkylphosphynotioyl group (e.g., dimethylphosphynotioyl group), a diarylphosphynotioyl group (e.g., diophenylphosphynotioyl group). A preferred protective group of hydroxyl group or hydroxymethyl group includes, for instance, a non-polymeric acyl group (specifically, a saturated $C_{2-6}$aliphatic acyl group etc., more specifically, a saturated $C_{2-4}$aliphatic acyl group etc.), a $C_{1-6}$alkoxy-carbonyl group, a carbamoyl group which may have a substituent.

A protective group for amino group includes, for example, protective groups same as the exemplified protective groups for hydroxyl group, such as t-butyl group, an aralkyl group, a non-polymerizable acyl group [e.g., a saturated aliphatic acyl group (e.g., a saturated $C_{2-6}$aliphatic acyl group, in particular a saturated $C_{2-4}$aliphatic acyl group), an aromatic acyl group (e.g., a $C_{7-13}$aromatic acyl group), an alicyclic acyl group], an alkoxy carbonyl group (e.g., a $C_{1-6}$alkoxycarbonyl group), an aralkyloxy carbonyl group, a dialkylphosphinotioyl group, a diarylphosphinotioyl group. A preferred protective group of amino group includes, for example, a non-polymerizable acyl group [e.g., a saturated $C_{2-6}$aliphatic acyl group (especially, a saturated $C_{2-4}$aliphatic acyl group), a $C_{7-13}$aromatic acyl group], an alkoxy carbonyl group (especially, a $C_{1-6}$ alkoxy-carbonyl group).

Examples of an N-substituted amino group include a mono- or di-$C_{1-6}$alkylamino group such as methylamino group, ethylamino group, propylamino group, dimethylamino group, diethylamino group (preferably, a mono- or di-$C_{1-4}$alkylamino group).

A protective group for a carboxyl group includes, for instance, an alkoxy group (e.g., a $C_{1-10}$alkoxy group such as methoxy, ethoxy, propoxy, isopropoxy, butoxy, isobutoxy, s-butoxy, t-butoxy and hexyloxy group; preferably a $C_{1-6}$alkoxy group, especially a $C_{1-4}$alkoxy group), a cycloalkyloxy group (e.g., cyclohexyloxy group), an aryloxy group (e.g., phenoxy group), an aralkyloxy group (e.g., benzyloxy group, diphenylmethyloxy group), a trialkylsilyloxy group (e.g., trimethylsilyloxy group), an amino group which may have a substituent [amino group; an N-substituted amino group (e.g., a mono- or di-$C_{1-6}$ alkylamino group such as methylamino, dimethylamino ethylamino and diethylamino group)], hydrazino group, an alkoxycarbonylhydrazino group (e.g., t-butoxycarbonylhydrazino group), an aralkylcarbonylhydrazino group (e.g., benzyloxycarbonylhydrazino group). A preferred protective group of carboxyl group includes an alkoxy group (especially, a $C_{1-6}$-alkoxy group), an amino group which may have a substituent (e.g., an N-substituted amino group, especially, a mono- or di-$C_{1-6}$alkylamino group).

An alkyl group includes, for instance, a $C_{1-6}$alkyl group such as methyl, ethyl, propyl, isopropyl, butyl, isobutyl, s-butyl, t-butyl and hexyl group (preferably, a $C_{1-4}$alkyl group, more preferably, methyl group or ethyl group).

Preferred examples of $X^1$ include hydroxyl group, a saturated $C_{2-6}$aliphatic acyloxy group (corresponding to a hydroxyl group protected by a saturated $C_{2-6}$aliphatic acyl group), a $C_{1-6}$alkoxy-carbonyloxy group (corresponding to a hydroxyl group protected by a $C_{1-6}$alkoxy-carbonyl group), a carbamoyloxy group which may have a substituent, (corresponding to a hydroxyl group protected by a carbamoyl group which may have a substituent).

Preferred examples of $X^2$ include nitro group, amino group, a $C_{2-6}$acylamino group (corresponding to an amino group protected by a $C_{2-6}$acyl group), a $C_{1-6}$alkoxycarbonylamino group (corresponding to an amino group protected by a $C_{1-6}$alkoxy-carbonyl group), a saturated $C_{2-6}$aliphatic acyloxy group (corresponding to a hydroxyl group protected by a saturated $C_{2-6}$aliphatic acyl group), a $C_{1-6}$alkoxy-carbonyloxy group (corresponding to a hydroxyl group protected by a $C_{1-6}$alkoxy-carbonyl group), a carbamoyl group which may have a substituent (corresponding to a hydroxyl group protected by a carbamoyl group which may have a substituent), carboxyl group, a $C_{1-10}$alkoxy-carbonyl group (corresponding to a carboxyl group protected by a $C_{1-10}$alkoxy group) (especially, a $C_{1-6}$alkoxy-carbonyl group), a carbamoyl group which may have a substituent (corresponding to a carboxyl group protected by an amino group which may have a substituent), hydroxymethyl group, isocyanato group.

Preferred examples of $X^3$ and $X^4$, depending on the species of $X^2$, include a hydrogen atom, an alkyl group, nitro group, amino group, a $C_{2-6}$acylamino group, a $C_{1-6}$alkoxycarbonylamino group, a saturated $C_{2-6}$aliphatic acyloxy group, a $C_{1-6}$alkoxy-carbonyloxy group, a carbamoyloxy group which may have a substituent, carboxyl group, a $C_{1-10}$alkoxy-carbonyl group (specifically, a $C_{1-6}$alkoxycarbonyl group), a carbamoyl group which may have a substituent, hydroxymethyl group, isocyanato group.

In the present specification, it is sometimes described as follows: OH for a hydroxyl group which may be protected by a protective group, OAc for a non-polymerizable acyloxy group, $NO_2$ for nitro group, $NH_2$ for an amino group or N-substituted amino group which may be protected by a protective group, COOH for a carboxyl group which may be protected by a protective group, $CH_2OH$ for a hydroxymethyl group which may be protected by a protective group, NCO for isocyanato group, H for a hydrogen atom, and R for an alkyl group.

An adamantane derivative shown by the formula (1) is a novel compound. A combination of $X^2$, $X^3$ and $X^4$ includes combinations of the following (1a), (2a), (3a), (4a), (5a) and (6a).

(1a) When $X^2$ is an $NO_2$ and $X^1$ is a hydroxyl group, $X^3$ and $X^4$ are not H, simultaneously. That is, [1] $X^1$ is a hydroxyl group, either $X^3$ or $X^4$ is H and the other is a functional group selected from R, $NO_2$, OH, $NH_2$, COOH, $CH_2OH$ and NCO, [2] $X^1$ is a hydroxyl group, $X^3$ and $X^4$ are functional groups selected from R, $NO_2$, OH, $NH_2$, COOH, $CH_2OH$ and NCO, or [3] $X^1$ is a hydroxyl group protected by a protective group, $X^3$ and $X^4$ are functional groups selected from H, R, $NO_2$, OH, $NH_2$, COOH, $CH_2OH$ and NCO.

(2a) When $X^2$ is an $NH_2$ and $X^1$ is a hydroxyl group, $X^3$ and $X^4$ are not H or R, simultaneously. That is, [1] $X^1$ is a hydroxyl group, either $X^3$ or $X^4$ is H and the other is a functional group selected from R, $NH_2$, OH, COOH, $CH_2OH$ and NCO, [2] $X^1$ is a hydroxyl group, either $X^3$ or $X^4$ is an R and the other is a functional group selected from $NH_2$, OH, COOH, $CH_2OH$ and NCO, [3] $X^1$ is a hydroxyl group, $X^3$ and $X^4$ are functional groups selected from $NH_2$, OH, COOH, $CH_2OH$ and NCO, or [4] $X^1$ is a hydroxyl group protected by a protective group, $X^2$ is an $NH_2$, $X^3$ and $X^4$ are functional groups selected from H, R, $NH_2$, OH, COOH, $CH_2OH$ and NCO.

(3a) When $X^2$ is an OH, $X^1$ is a hydroxyl group or a saturated aliphatic acyloxy group and $X^2$ is a hydroxyl group or a saturated aliphatic acyloxy group, $X^3$ and $X^4$ are not H or R, simultaneously. Incidentally, when $X^1$ and $X^2$ are both hydroxyl groups, $X^3$ and $X^4$ are not a combination of a hydrogen atom and a carboxyl group which may be protected by a protective group. That is, [1] $X^1$ and $X^2$ are both hydroxyl groups, either $X^3$ or $X^4$ is H and the other is a functional group selected from R, OH, $CH_2OH$ and NCO, [2] $X^1$ and $X^2$ are both hydroxyl groups, either $X^3$ or $X^4$ is R and the other is a functional group selected from OH, COOH, $CH_2OH$ and NCO, [3] $X^1$ and $X^2$ are both hydroxyl groups, $X^3$ and $X^4$ are functional groups selected from OH, COOH, $CH_2OH$ and NCO, [4] $X^1$ and $X^2$ are both hydroxyl groups protected by saturated aliphatic acyl groups, either $X^3$ or $X^4$ is H and the other is a functional group selected from R, OH, COOH, $CH_2OH$ and NCO, [5] $X^1$ and $X^2$ are both hydroxyl groups protected by saturated aliphatic acyl groups, either $X^3$ or $X^4$ is R and the other is a functional group selected from OH, COOH, $CH_2OH$ and NCO, [6] either $X^1$ or $X^2$ is hydroxyl group and the other is a hydroxyl group protected by a saturated aliphatic acyl group, either $X^3$ or $X^4$ is H and the other is a functional group selected from R, OH, COOH, $CH_2OH$ and NCO, [7] either $X^1$ or $X^2$ is hydroxyl group and the other is a hydroxyl group protected by a saturated aliphatic acyl group, either $X^3$ or $X^4$ is R and the other is a functional group selected from OH, COOH, $CH_2OH$ and NCO, or [8] $X^1$ and $X^2$ are hydroxyl groups protected by protective groups excluding saturated aliphatic acyl groups, $X^3$ and $X^4$ are functional groups selected from H, R, OH, COOH, $CH_2OH$ and NCO.

(4a) When $X^2$ is COOH and $X^1$ is hydroxyl group or a saturated aliphatic acyloxy group, $X^3$ and $X^4$ are not simultaneously H or R, and not a combination of H and R. That is, [1] $X^1$ is hydroxyl group or a hydroxyl group protected by a saturated aliphatic acyl group, either $X^3$ or $X^4$ is H or R and the other is a functional group selected from COOH, $CH_2OH$ and NCO, [2] $X^1$ is a hydroxyl group protected by a protective group excluding a saturated aliphatic acyl group, $X^3$ and $X^4$ are functional groups selected from H, R, COOH, $CH_2OH$ and NCO.

(5a) When $X^2$ is $CH_2OH$ and $X^1$ is hydroxyl group, $X^3$ and $X^4$ are not H, simultaneously. That is, [1] $X^1$ is hydroxyl group, X is $CH_2OH$, $X^3$ is H, and $X^4$ is a functional group selected from R, $CH_2OH$ and NCO, [2] $X^1$ is hydroxyl group, X is $CH_2OH$, $X^3$ and $X^4$ are functional groups selected from R, $CH_2OH$ and NCO, [3] $X^1$ is a hydroxyl group protected by a protective group, X is $CH_2OH$, $X^3$ and $X^4$ are functional groups selected from H, R, $CH_2OH$ and NCO.

(6a) When $X^2$ is isocyanato group and $X^1$ is a hydroxyl group, $X^3$ and $X^4$ are not H, simultaneously. That is, [1] $X^1$ is hydroxyl group, $X^2$ is NCO, $X^3$ is H, and $X^4$ is a functional group selected from R and NCO, [2] $X^1$ is hydroxyl group, $X^2$ is NCO, $X^3$ and $X^4$ are functional groups selected from R and NCO, [3] $X^1$ is a hydroxyl group protected by a protective group, $X^2$ is NCO, $X^3$ and $X^4$ are functional groups selected from H, R and NCO.

Such a novel adamantane derivative includes an adamantane derivative having at least one kind of functional groups selected from nitro group, amino group, hydroxyl group, carboxyl group, hydroxymethyl group and isocyanato group, together with a hydroxyl group. Incidentally, hydroxyl group, amino group, carboxyl group or hydroxymethyl group may be protected by a protective group, a nitrogen atom of an amino group may have one or two substituents. Further, an adamantane derivative having an acidic group or a basic group may form a salt thereof.

As an adamantane derivative containing a nitro group, there may be exemplified a monool body such as 1-nitro-3-methyl-5-adamantanol, 1-nitro-3,5-dimethyl-7-adamantanol, 1,3-dinitro-5-adamantanol, 1,3-dinitro-5-methyl-7-adamantanol, 1,3,5-trinitro-7-adamantanol, 1-carboxy-3-nitro-5-adamantanol, 1-acetylamino-3-nitro-5-adamantanol, 1-hydroxymethyl-3-nitro-5-adamantanol; a diol body such as 1-nitro-3,5-adamantanediol, 1-nitro-3-methyl-5,7-adamantanediol, 1,3-dinitro-5,7-adamantanediol; a triol body such as 1-nitro-3,5,7-adamantanetriol; an adamantanol derivative containing a nitro group, in which a hydroxyl group is protected by a protective group [such as a saturated aliphatic acyl group (e.g., a saturated $C_{2-6}$aliphatic acyl group), an alkoxycarbonyl group (e.g., a $C_{1-6}$alkoxy-carbonyl group), a carbamoyl group which may have a substituent], such as 1-acetoxy-3-nitroadamantane, 1-methoxycarbonyloxy-3-nitroadamantane, 1,3-bis(methoxycarbonyloxy)-5-nitroadamantane, 1-(N-methylcarbamoyloxy)-3-nitroadamantane.

An adamantane derivative having an amino group includes, for example, an adamantanol derivative having a non-substituted amino group which is not protected by a protective group (e.g., a monool body such as 1-amino-3-methyl-5-adamantanol, 1,3-diamino-5-adamantanol, 1,3-diamino-5-methyl-7-adamantanol, 1,3,5-triamino-7-adamantanol; a diol body such as. 1-amino-3,5-adamantanediol, 1-amino-3-methyl-5,7-adamantanediol, 1,3-diamino-5,7-adamantanediol; a triol body such as 1-amino-3,5,7-adamantanetriol), an adamantanol derivative having an N-substituted amino group (e.g., a monool body such as 1-methylamino-3-methyl-5-adamantanol, 1,3-bis(methylamino)-5-adamantanol, 1,3-bis(ethylamino)-5-adamantanol, 1,3-bis(dimethylamino)-5-adamantanol, 1,3-bis(diethylamino)-5-adamantanol, 1,3-bis(methylamino)-5-methyl-7-adamantanol, 1,3,5-tris(methylamino)-7-adamantanol, 1,3,5-tris(dimethylamino)-7-adamantanol; a diol body such as 1-methylamino-3,5-adamantanediol, 1-ethylamino-3,5-adamantanediol, 1-dimethylamino-3,5-adamantanediol, 1-diethylamino-3,5-adamantanediol, 1-methylamino-3-methyl-5,7-adamantanediol, 1,3-bis(methylamino)-5,7-adamantanediol, 1,3-bis(ethylamino)-5,7-adamantanediol, 1,3-bis(dimethylamino)-5,7-adamantanediol, 1,3-bis(diethylamino)-5,7-adamantanediol; a triol body such as 1-methylamino-3,5,7-adamantanetriol, 1-dimethylamino-3,5,7-adamantanetriol), an adamantanol derivative having an amino group protected by a protective group [an alcohol body of an adamantane having a $C_{2-6}$acylamino group, for example, a monool body such as 1-acetylamino-3-methyl-5-adamantanol, 1,3-bis(acetylamino)-5-adamantanol, 1,3-bis(acetylamino)-5-methyl-7-adamantanol, 1,3,5-tris(acetylamino)-7-adamantanol; a diol body such as 1acetylamino-3,5-adamantanediol, 1-acetylamino-3-methyl-5,7-adamantanediol, 1,3-bis(acetylamino)-5,7-adamantanediol; a triol body such as 1-acetylamino-3,5,7-adamantanetriol], an adamantanol derivative having an amino group in which a hydroxyl group is protected by a protective group such as a saturated aliphatic acyl group (e.g., a saturated $C_{2-6}$aliphatic acyl group), an alkoxycarbonyl group (e.g., a $C_{1-6}$alkoxy-carbonyl group), a carbamoyl group which may have a substituent, [e.g., 1-acetoxy-3-aminoadamantane, 1-acetoxy-3-acetylaminoadamantane, 1-methoxycarbonyloxy-3-aminoadamantane, 1-acetylamino-3-methoxycarbonyloxyadamantane, 1,3-bis(methoxycarbonyloxy)-5-aminoadamantane, 1-(N-methylcarbamoyloxy)-3-aminoadamantane].

Examples of an adamantane derivative having plural hydroxyl groups include an adamantanepolyol derivative having a carboxyl group such as 1-carboxy-3-methyl-5,7-adamantanediol, 1,3-dicarboxy-5,7-adamantanediol, 1-methoxycarbonyl-3-methyl-5,7-adamantanediol, 1-ethoxycarbonyl-3-methyl-5,7-adamantanediol, 1,3-di(methoxycarbonyl)-5,7-adamantanediol, 1,3-di(ethoxycarbonyl)-5,7-adamantanediol, 1-carboxy-3,5,7-adamantanetriol, 1-ethoxycarbonyl-3,5,7-adamantanetriol, 1-methoxycarbonyl-3,5,7-adamantanetriol; an adamantanepolyol derivative having an acyloxy group (e.g., a saturated $C_{2-6}$aliphatic acyloxy group) such as 1-acetyloxy-3-methyl-5-adamantanol, 1,3-bis(acetyloxy)-5-adamantanol, 1,3-bis(acetyloxy)-5-methyl-7-adamantanol, 1,3,5-tris(acetyloxy)-7-adamantanol, 1-acetyloxy-3,5-adamantanediol, 1-acetyloxy-3-methyl-5,7-adamantanediol, 1,3-bis(acetyloxy)-5,7-adamantanediol, 1-acetyloxy-3,5,7-adamantanetriol, 1-acetyloxy-3-methoxycarbonyloxyadamantane, 1-acetyloxy-3-(N-methylcarbamoyloxy)adamantane, 1,3,5-tris(acetyloxy)adamantane; an adamantanepolyol derivative having an alkoxycarbonyloxy group (e.g., a $C_{1-6}$alkoxycarbonyloxy group) such as 1-methoxycarbonyloxy-3-adamantanol, 1-methoxycarbonyloxy-3,5-adamantanediol, 1,3-bis(methoxycarbonyloxy)-5-adamantanol, 1-(N-methylcarbamoyloxy)-3-methoxycarbonyloxyadamantane, 1,3-bis(methoxycarbonyloxy)adamantane, 1,3,5-tris(methoxycarbonyloxy)adamantane, 1-carboxy-3,5-bis(N-methylcarbamoyloxy)adamantane; an adamantanepolyol derivative having carbamoyloxy group which may have a substituent, such as 1-(N-methylcarbamoyloxy)-3-adamantanol, 1-(N-methylcarbamoyloxy)-3,5-adamantanediol, 1,3-bis(N-methylcarbamoyloxy)-5-adamantanol, 1,3-bis(N-methylcarbamoyloxy)adamantane, 1,3,5-tris(N-methylcarbamoyloxy)adamantane.

An adamantane derivative having a carboxyl group includes, for example, an adamantanol derivative having a carboxyl group protected by no protective group (an alcohol body of an adamantane having a carboxyl group such as a monool body e.g., 1,3-dicarboxy-5-adamantanol, 1,3-dicarboxy-5-methyl-7-adamantanol, 1,3,5-tricarboxy-7-adamantanol), an adamantanol derivative having a carboxyl group protected by a protective group [an alcohol body of an adamantane having a $C_{1-10}$alkoxy-carbonyl group such as a monool body e.g., 1,3-bis(methoxycarbonyl)-5-adamantanol, 1,3-bis(ethoxycarbonyl)-5-adamantanol, 1,3-bis(methoxycarbonyl)-5-methyl-7-adamantanol, 1,3-bis(ethoxycarbonyl)-5-methyl-7-adamantanol, 1,3,5-tris(methoxycarbonyl)-7-adamantanol, 1-(N,N-dimethylcarbamoyl)-3-adamantanol], an adamantanol derivative having a carboxyl group in which a hydroxyl group is protected by a protective group such as a saturated aliphatic acyl group (e.g., a saturated $C_{2-6}$-aliphatic acyl group), an alkoxycarbonyl group (e.g., a $C_{1-6}$alkoxycarbonyl group), a carbamoyl group which may have a substituent [e.g., 1-acetoxy-3-methoxycarbonyladamantane, 1-acetoxy-3-(N,N-dimethylcarbamoyl)adamantane, 1-carboxy-3-methoxycarbonyloxyadamantane, 1-methoxycarbonyl-3-methoxycarbonyloxyadamantane, 1-(N,N-dimethylcarbamoyl)-3-methoxycarbonyloxyadamantane, 1-(N,N-dimethylcarbamoyl)-3-(N-methylcarbamoyloxy)adamantane, 1-carboxy-3-(N-methylcarbamoyloxy)adamantane, 1-methoxycarbonyl-3-(N-methylcarbamoyloxy)adamantane].

An adamantane derivative having a hydroxymethyl group includes, for instance, an adamantanol derivative having an alkyl group and a hydroxymethyl group such as 1-hydroxymethyl-3-methyl-5-adamantanol; an adamantanol derivative having plural hydroxymethyl groups such as 1,3-bis(hydroxymethyl)-5-adamantanol; an adamantanol derivative having a hydroxymethyl group in which a hydroxyl group bound to the adamantane backbone is protected by a protective group such as a saturated aliphatic acyl group (e.g., a saturated $C_{2-6}$aliphatic acyl group), an alkoxycarbonyl group (e.g., a $C_{1-6}$alkoxy-carbonyl group), a carbamoyl group which may have a substituent, such as 1-acetoxy-3-hydroxymethyladamantane, 1-hydroxymethyl-3-methoxycarbonyloxyadamantane, 1-hydroxymethyl-3-(N-methylcarbamoyl)adamantane.

An adamantane derivative having an isocyanate group includes, for example, an adamantanol derivative having an alkyl group and an isocyanato group such as 1-isocyanato-3-methyl-5-adamantanol derivative having plural isocyanato groups such as 1,3-diisocyanato-5-adamantanol; an adamantanol derivative having an isocyanato group in which a hydroxyl group is protected by a protective group such as a saturated aliphatic acyl group (e.g., a saturated $C_{2-6}$aliphatic acyl group), such as 1-acetoxy-3-isocyanatoadamantane.

The adamantane derivative shown by the formula (1), depending on the species of $X^2$, may have a different substituent such as a halogen atom, an oxo group, a hydroxyalkyl group (e.g., a hydroxy $C_{2-4}$alkyl group such as 2-hydroxyethyl group), an acyl group (e.g., a $C_{1-6}$acyl group such as formyl, acetyl, propionyl, butyryl, isobutyryl, valeryl, isovaleryl and pivaloyl group), an alkoxycarbonyl group (e.g., a $C_{1-6}$alkoxy-carbonyl gruop such as methoxycarbonyl, ethoxycarbonyl, propoxycarbonyl, isopropoxycarbonyl, butoxycarbonyl, isobutoxycarbonyl, t-butoxycarbonyl and hexylcarbonyl group), a cyano group.

The adamantane derivative shown by the formula (1) can be produced through an oxidation step (especially, an oxidation step by oxygen using an imide compound (2) described below). The adoption of the oxidation step by oxygen using the imide compound realized on efficient production of not only the novel adamantane derivative but also the known adamantane derivatives.

According to the formula (1), the known adamantane derivatives correspond to the following compounds (1b) to (4b) in which $X^1$ to $X^4$ are as follows:

(1b) a compound in which $X^1$ is hydroxyl group and $X^3$ and $X^4$ are both H when $X^2$ is $NO_2$ (2b) a compound in which $X^1$ is hydroxyl group and $X^3$ and $X^4$ are both H or both R when $X^2$ is NH2

(3b) a compound in which, when $X^2$ is OH, [1] $X^1$ is hydroxyl group or a saturated aliphatic acyloxy group, $X^2$ is hydroxyl group or a saturated aliphatic acyloxy group, both $X^3$ and $X^4$ are H or R, and [2] both $X^1$ and $X^2$ are hydroxyl groups, either $X^3$ or $X^4$ is H and the other is COOH (4b) a compound in which, when $X^2$ is COOH, $X^1$ is hydroxyl group or a saturated aliphatic acyloxy group, $X^3$ and $X^4$ are functional groups selected from an H and an R (5b) a compound in which, when $X^2$ is $CH_2OH$, $X^1$ is hydroxyl group and both $X^3$ and $X^4$ are H (6b) a compound in which, when $X^2$ is NCO, $X^1$ is hydroxyl group, both $X^3$ and $X^4$ are H.

Such known adamantane derivatives include, for example, an adamantane derivative having a nitro group (e.g., 1-nitro-3-adamantanol), an adamantane derivative having an amino group (e.g., an alcohol body of an adamantane having a $C_{2-6}$acylamino group such as 1-amino-3-adamantanol, 1-amino-3,5-dimethyl-7-adamantanol, 1-methylamino-3-admantanol, 1-acetylamino-3-adamantanol, 1-dimethylamino-3-adamantanol, 1-acetylamino-3,5-dimethyl-7-adamantanol; an alcohol body of an adamantane having a $C_{1-6}$alkoxy-carbonylamino group such as 1-methoxycarbonylamino-3-adamantanol), an adamantanepolyol derivative (e.g., 1,3-adamantanediol, 1,3,5-adamantanetriol), and adamantane derivative having a saturated aliphatic acyloxy group (e.g., an alcohol body of an adamantane having a $C_{2-6}$acyloxy group such as 1-acyloxy-3-adamantanol, 1-acyloxy-3,5-dimethyl-7-adamantanol), an adamantane derivative having a carboxyl group (e.g., an alcohol body of an adamantane having a $C_{1-10}$alkoxy-carbonyl group such as 1-carboxy-3-adamantanol, 1-carboxy-3-methyl-5-adamantanol, 1-carboxy-3,5-dimethyl-7-adamantanol, 1-carboxy-3,5-adamantanediol, 1-methoxycarbonyl-3-adamantanol, 1-methoxycarbonyl-3-methyl-5-adamantanol, 1-methoxycarbonyl-3,5-dimethyl-7-adamantanol, 1-methoxycarbonyl-3,5-adamantanediol), an adamantane derivative having a hydroxymethyl group (e.g., 1-hydroxymethyl-3-adamantanol), an adamantane derivative having an isocyanato group (e.g., 1-isocyanato-3-adamantanol).

[Production Process]

The adamantane derivative shown by the formula (1) and the known adamantane derivative, that is, the adamantane derivative having a hydroxyl group and a functional group can be produced by subjecting an adamantane derivative shown by the following formula (1a):

(1a)

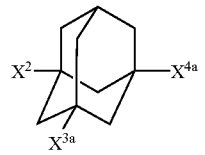

wherein $X^2$ represents nitro group, a hydroxyl group which may be protected by a protective group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group; $X^{3a}$ and $X^{4a}$ may be the same or different from each other and each may represent a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanato group; to at least one step selected from the following oxidation step (i), nitration step (ii) and carboxylation step (iii):

(i) an oxidation step by oxygen in the presence of a catalyst comprising an imide compound shown by the formula (2):

(2)

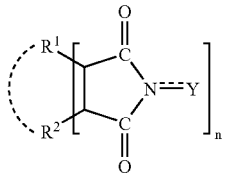

wherein $R^1$ and $R^2$ may be the same or different from each other and each may represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond or an aromatic or non-aromatic ring; Y represents an oxygen atom or a hydroxyl group; and n denotes an integer of 1 to 3

(ii) at least one nitration step selected from the following steps (iia), (iib) and (iic):

(iia) a nitration step by a nitrogen oxide in the presence of a catalyst comprising an imide compound shown by the formula (2);

(iib) a nitration step by oxygen and at least one nitrogen oxide selected from dinitrogen oxide and nitrogen monoxide; and (iic) a nitration step by nitrogen dioxide (iii) a carboxylation step by carbon monoxide and oxygen in the presence of a catalyst comprising an imide compound shown by the formula (2).

An amino group, hydroxymethyl group and the like may be formed by subjecting the adamantane (1a) to the nitration step and/or carboxylation step followed by a reduction step. The formed amino group may be converted into an isocyanato group by using a conventional method.

More practically, the adamantane derivative can be obtained in accordance with the following reaction step schemes (I) to (V).

The adamantane derivative having a nitro group or an amino group (comprising an amino group protected by a protective group) together with a hydroxyl group (comprising a hydroxyl group protected by a protective group) can be obtained in accordance with, for example, the following reaction step scheme (I).

Reaction step scheme (I)

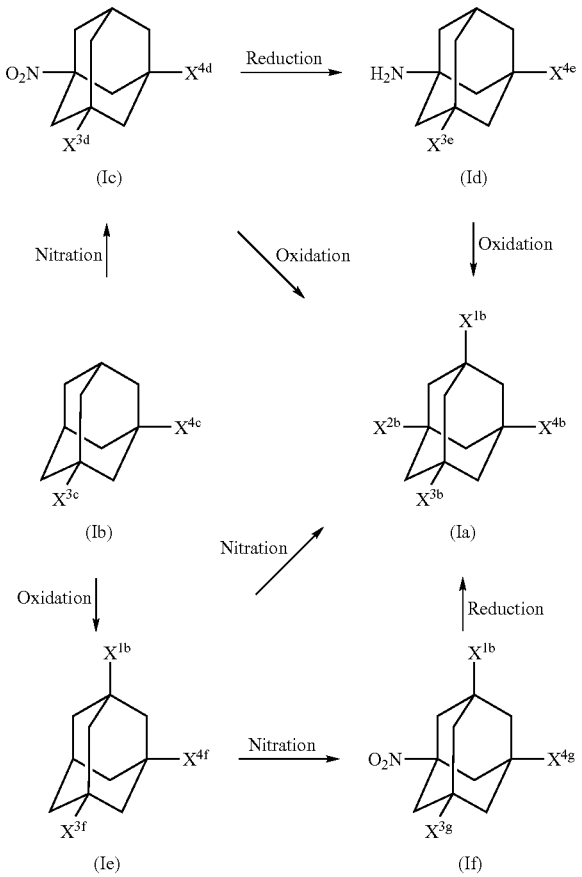

Wherein $X^{1b}$ represents OH, $X^{2b}$ represents $NO_2$ or $NH_2$; $X^{3b}$, $X^{4b}$, $X^{3c}$, $X^{4c}$, $X^{3d}$, $X^{4d}$, $X^{3e}$, $X^{4e}$, $X^{3f}$, $X^{4f}$, $X^{3g}$ and $X^{4g}$ may be the same or different from each other and represent H, R, $NO_2$, OH, $NH_2$, COOH, $CH_2OH$ or NCO.

[Nitration Reaction]

A nitration reaction in the reaction step scheme (I), [a nitration reaction which derives the compound (Ic) derives from the compound (Ib), a nitration reaction which provides the compound (Ia) or (If) from the compound (Ie)], can be carried out by a conventional method [for example, a method using a nitrating agent (e.g., mixed acid of sulfuric acid and nitric acid, nitric acid, nitric acid and an organic acid (e.g., a carboxylic acid such as acetic acid), nitric acid salt and sulfuric acid, dinitrogen pentoxide etc.)]. Examples of a preferred nitration process include [1] a nitration process which comprises contacting a substrate [the compound (Ib) or the compound (Ie)] with nitrogen oxide in the presence of a catalyst system comprising an imide compound (2) and a co-catalyst described below, [2] a nitrating process of the substrate using oxygen and at least one nitrogen compound selected from dinitrogen oxide and nitrogen monoxide in the absence of a catalyst, and [3] a nitration process which comprises contacting nitrogen dioxide with the substrate.

The compound (Ib) includes, for example, adamantane, an adamantane having an alkyl group (e.g., an adamantane having an alkyl group which has one to six carbon atoms such as 1-methyladamantane, 1,3-dimethyladamantane, 1-ethyladamantane, 1-propyladamantane, 1-isopropyladamantane, 1-butyladamantane), an adamantane which has one or more nitro groups previously (e.g., 1-nitroadamantane, 1,3-dinitroadamantane), an adamantane having a carboxyl group (e.g., 1-carboxyadamantane), an adamantane having a hydroxymethyl group (e.g., 1-hydroxymethyladamantane). As the compound (Ib), use may be practically made of adamantane, an adamantane having an alkyl group which has one to four carbon atoms (preferably, an adamantane having an alkyl group which has one to two carbon atoms, especially, an adamantane having a methyl group). By subjecting the compound (Ib) to a nitration reaction, the compound (Ic) can be obtained. For instance, when adamantane of the compound (Ib) is subjected to the nitration, 1-nitroadamantane, 1,3-dinitroadamantane, 1,3,5-trinitroadamantane can be obtained.

The compound (Ie) includes, for example, an adamantane having a hydroxyl group such as 1-adamantanol, 3-methyl-1-adamantanol, 3,5-dimethyl-1-adamantanol, 1,3-adamantanediol, 5-methyl-1,3-adamantanediol, 1,3,5-adamantanetriol. When the compound (Ie) is subjected to the nitration reaction, the compound (Ia) or (If) can be obtained. For example, when 1-adamantanol of the compound (Ie) is subjected to the nitration reaction, 1-nitro-3-adamantanol, 1,3-dinitro-5-adamantanol, 1,3,5-trinitro-7-adamantanol etc can be obtained. Moreover, when 1,3-adamantanediol as a substrate is subjected to the nitration reaction, 1-nitro-3,5-adamantanediol, 1,3-dinitro-5,7-adamantanediol etc can be obtained. When 1,3,5-adamantanetriol as a substrate is subjected to the nitration reaction, 1-nitro-3,5,7-adamantanetriol etc can be obtained.

[Catalyst Comprising an Imide Compound]

In the imide compound shown by the formula (2), a halogen atom as the substituents $R^1$ and $R^2$ includes iodine, bromine, chlorine and fluorine atoms. An alkyl group includes, for example, a straight chain or branched chain alkyl group having about 1 to 10 carbon atoms such as methyl, ethyl, propyl, isopropyl, butyl, isobutyl, sec-butyl, t-butyl, pentyl, hexyl, heptyl, octyl and decyl group. Preferred examples of an alkyl group include an alkyl group having about 1 to 6 carbon atoms, in particular a lower alkyl group having about 1 to 4 carbon atoms.

An aryl group includes, for instance, phenyl group and naphthyl group. A cycloalkyl group includes, for example, cyclopentyl, cyclohexyl, and cyclooctyl group.

An alkoxy group includes, for example, an alkoxy group having about 1 to 10 carbon atoms such as methoxy, ethoxy, propoxy, isopropoxy, butoxy, isobutoxy, t-butoxy, pentyloxy and hexyloxy group and preferably an alkoxy group having about 1 to 6 carbon atoms, in particular a lower alkoxy group having about 1 to 4 carbon atoms. An alkoxycarbonyl group includes, for example, an alkoxycarbonyl group having about 1 to 10 carbon atoms in the alkoxy moiety such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl and hexyloxycarbonyl group. A preferred alkoxycarbonyl group includes an alkoxycarbonyl group having about 1 to 6 carbon atoms in the alkoxy moiety, specifically a lower alkoxycarbonyl group having about 1 to 4 carbon atoms in the alkoxy moiety.

As an acyl group, there may be exemplified an acyl group having about 1 to 6 carbon atoms such as formyl, acetyl, propionyl, butyryl, isobutyryl, valeryl, isovaleryl and pivaloyl group.

The substituents $R^1$ and $R^2$ may be either the same or different from each other. In the formula (2), $R^1$ and $R^2$ may bond together to form a double bond, or an aromatic or non-aromatic ring. A preferred aromatic or non-aromatic ring may be a 5- to 12-membered ring, in particular a 6- to 10-membered ring. Such a ring may be a heterocyclic ring or a condensed heterocyclic ring, but it may be practically a hydrocarbon ring. Such rings includes, for instance, a non-aromatic alicyclic ring (e.g., a cycloalkane ring which may have a substituent such as cyclohexane ring, a cycloalkene ring which may have a substituent such as cyclohexene ring), a non-aromatic bridged (cross-linked) ring (e.g., a bridged hydrocarbon ring which may have a substituent such as 5-norbornene ring), an aromatic ring which may have a substituent such as benzene ring, naphthalene ring. The ring may practically comprise an aromatic ring.

A preferred imide compound includes compounds shown by the following formulae (2a) to (2f), (2a)

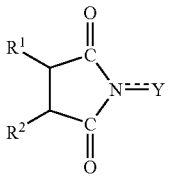

(2b)

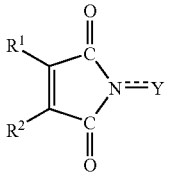

-continued (2c)

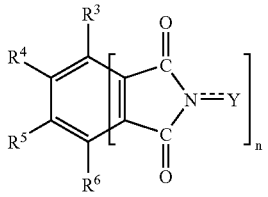

(2d)

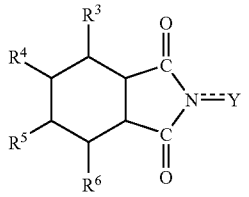

(2e)

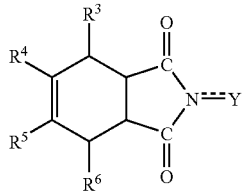

(2f)

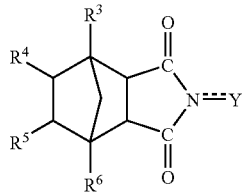

wherein $R^3$ to $R^6$ may be the same or different from each other, and each may represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$, Y and n have the same meanings as defined above.

In the substituents $R^3$ to $R^6$, an alkyl group includes alkyl groups similar to those exemplified in the paragraphs of $R^1$ and $R^2$, in particular an alkyl group having about 1 to 6 carbon atoms. An alkoxy group includes the same alkoxy groups as mentioned above, in particular a lower alkoxy group having about 1 to 4 carbon atoms. An alkoxycarbonyl group includes the same alkoxycarbonyl gruops as mentioned above, especially, a lower alkoxycarbonyl group having about 1 to 4 carbon atoms in the alkoxy moiety. As an acyl group, there may be exemplified the same acyl groups as mentioned above, especially an acyl group having about 1 to 6 carbon atoms. As a halogen atom, there may be exemplified fluorine, chlorine and bromine atom. The substituents $R^3$ to $R^6$ may be practically a hydrogen atom, a lower alkyl group having about 1 to 4 carbon atoms, a carboxyl group, a nitro group or a halogen atom.

In the formula (2), the symbol Y represents oxygen atom or hydroxyl group, and n is usually about 1 to 3, preferably 1 or 2. The imide compound shown by the formula (2) can be used singly or in combination of two or more.

An acid anhydride corresponding to the imide compound shown by the formula (2) includes, for example, a saturated or unsaturated aliphatic polycarboxylic acid anhydride such as succinic anhydride, maleic anhydride; a saturated or unsaturated non-aromatic cyclicpolycarboxylic acid anhydride (an alicyclic polycarboxylic acid anhydride) such as tetrahydrophthalic anhydride, hexahydrophthalic anhydride (1,2-cyclohexanedicarboxylic anhydride), 1,2,3,4-cyclohexanetetracarboxylic acid 1,2-anhydride; a bridged cyclic polycarboxylic anhydride (an alicyclic polycarboxylic anhydride) such as hetic anhydride, himic anhydride; an aromatic polycarboxylic acid anhydride such as phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8:4,5-naphthalenetetracarboxylic dianhydride.

As a preferred imide compound, there may be mentioned, for example, an imide compound derived from an aliphatic polycarboxylic acid anhydride (e.g., N-hydroxysuccinimide, N-hydroxymaleimide), an imide compound derived from an alicyclic polycarboxylic acid anhydride or an aromatic polycarboxylic anhydride (e.g., N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide). A typically preferable imide compound includes an N-hydroxyimide compound derived from an alicyclic polycarboxylic anhydride, particularly from an aromatic polycarboxylic anhydride, such as N-hydroxyphthalimide.

The imide compound may be prepared by a conventional imidation reaction, for example, by reating a corresponding acid anhydride with hydroxylamine $NH_2OH$ to ring-open an acid anhydride group followed by ring-closing and imidating.

A catalyst comprising an imide compound shown by the formula (2) may be whichever of a homogeneous system or a heterogeneous system. Moreover, the catalyst may be a solid catalyst comprising a catalytic component supported on a support or carrier, as well. As the support, use can be practically made of a porous support such as activated carbon, zeolite, silica, silica-alumina, bentonite. As for a supported amount of the catalytic component in the solid catalyst, the amount of the imide compound shown by the formula (2) is about 0.1 to 50 parts by weight, preferably about 0.5 to 30 parts by weight and more preferably about 1 to 20 parts by weight relative to 100 parts by weight of the support.

[Nitrogen Oxide]

A nitrogen oxide employed in the nitration reaction is shown by the formula (3) $N_nO_m$, wherein n denotes an integer of 1 or 2 and m denotes an integer of 1 to 6.

In the nitrogen oxide shown by the formula (3), when n is 1, m is usually an integer of 1 to 3 and when n is 2, m is usually an integer of 1 to 6.

As such nitrogen oxide, there may be exemplified $N_2O$, NO, $N_2O_3$, $NO_2$ (nitrogen dioxide), $N_2O_4$, $N_2O_5$, $NO_3$, $N_2O_6$. The nitrogen oxide can be employed singly or in combination of two or more.

A preferred nitrogen oxide includes, for instance, [1] a nitrogen oxide formed by a reaction of at least one nitrogen oxide selected from dinitrogen oxide ($N_2O$) and nitrogen monoxide (NO) with oxygen, specifically $N_2O_3$, or a nitrogen oxide containing $N_2O_3$ as a main component, or [2] nitrogen dioxide ($NO_2$) or a nitrogen oxide containing $NO_2$ as a main component.

$N_2O_3$ may be easily obtained by a reaction of $N_2O$ and/or NO with oxygen. Therefore, the nitration can be carried out by introducing $N_2O$ and/or NO and oxygen into the reaction system without forming $N_2O_3$ previously. Whichever of pure oxygen or oxygen diluted with an inert gas (e.g., carbon dioxide, nitrogen, helium or argon gas) may be used as oxygen. Air may be employed as an oxygen source. In the above case, even if the reaction is conducted in the absence of the catalyst, the corresponding nitro compound can be obtained in high yield. Moreover, also in the case where a substrate is contacted with nitrogen dioxide, a nitro compound can be produced in good yield, without using a catalyst.

The amount of the imide compound shown by the formula (2) may be selected within a wide range, for instance, within a range of about 0.001 mole (0.1 mole %) to 1 mole (100 mole %), preferably about 0.001 mole (0.1 mole %) to 0.5 mole (50 mole %), more preferably about 0.01 to 0.3 mole relative to 1 mole of a substrate. It may be practically selected within a range of about 0.01 to 0.25 mole relative to 1 mole of a substrate.

The imide compound (2) may constitute a catalyst system in combination with a co-catalyst of an oxidation catalyst described below. The species and the amount of the co-catalyst may be selected within the same ranges as those of a co-catalyst described below.

The amount of the nitrogen oxide can be selected according to the amount of nitro group introduced thereto, for example, within a range of about 1 to 50 mole, preferably about 1.5 to 30 mole, and is usually about 2 to 25 mole, relative to 1 mole of a substrate.

The nitration reaction is usually conducted in an organic solvent inert to the reaction. As the organic solvent, there may be mentioned, for example, an organic acid (e.g., a carboxylic acid such as formic acid, acetic acid, propionic acid; a hydroxycarboxylic acid such as oxalic acid, citric acid, tartaric acid; a sulfonic acid such as methanesulfonic acid, ethanesulfonic acid; and an arylsulfonic acid such as benzenesulfonic acid, p-toluenesulfonic acid), a nitrile (e.g., acetonitrile, propionitrile, benzonitrile), an amide (e.g., formamide, acetamide, dimethylformamide, dimethylacetamide), an alcohol (e.g., t-butanol, t-amyl alcohol), an aliphatic hydrocarbon (e.g., hexane, octane), an aromatic hydrocarbon (e.g., benzene), a halogenated hydrocarbon (e.g., chloroform, dichloromethane, dichloroethane, carbon tetrachloride, chlorobenzene), a nitro compound (e.g., nitrobenzene, nitromethane, nitroethane), an ester (e.g., a $C_{2-10}$aliphatic carboxylic acid-$C_{1-10}$alkyl ester such as ethyl acetate, butyl acetate, ethyl propionate; a carboxylic aryl ester such as phenyl acetate, phenyl propionate; a $C_{7-12}$aromatic carboxylic acid-$C_{1-10}$alkyl ester), methyl benzoate, dimethyl phthalate, an ether (e.g., dimethyl ether, diethylether, diisopropyl ether, dioxane, tetrahydrofuran), and mixtures of these solvents. Use may be practically made of, as the solvent, an organic acid (e.g., a carboxylic acid such as acetic acid), a nitrile (e.g., benzonitrile), a halogenated hydrocarbon (e.g., dichloroethane).

The use of the catalyst comprising the imide compound allows the nitration reaction to proceed smoothly even under comparatively mild or moderate conditions. The reaction temperature may be selected, according to the species of the imide compound or the substrate, for instance, within a range of about 0 to 150° C., preferably about 25 to 125° C., more preferably about 30 to 100° C. The nitration reaction can be carried out at ambient pressure (atmospheric pressure) or under a pressure (under a load).

[Oxidation Reaction]

For the oxidation reaction in the reaction step scheme (I) [an oxidation reaction which produces the compound (Ie)

from the compound (Ib), an oxidation reaction which leads the compound (Ic) or the compound (Id) to the compound (Ia)], an oxidation process of the substrate [the compound (Ib), the compound (Ic) or the compound (Id)] by oxygen in the presence of an oxidation catalyst comprising the imide compound shown by the formula (2) may be used.

When the compound (Ib) is subjected to the oxidation reaction (the oxidation process by oxygen) using the imide compound (2), the compound (Ie) can be obtained. For instance, oxidation of adamantane of the compound (Ib) provides 1-adamantanol, 1,3-adamantanediol and soon. The oxidation of 1-carboxyadamantane provides 1-carboxy-3-adamantanol and so forth.

The compound (Ic) includes, for example, 1-nitroadamantane, 1-nitro-3-methyladamantane, 1-nitro-3-5-dimethyladamantane, 1,3-dinitroadamantane, 1,3-dinitro-5-methyladamantane, 1,3,5-trinitroadamantane. When the oxidation process with oxygen using the oxidation catalyst comprising the imide compound is applied to the compound (Ic), an adamantane derivative in which $X^{2b}$ of the compound (Ia) is a nitro group [the compound having a nitro group (Ia)] can be obtained. For example, contact of 1-nitroadamantane of the compound (Ic) with oxygen in the presence of the imide compound shown by the formula (2), provides 1-nitro-3-adamantanol, 1-nitro-3,5-adamantanediol, 1-nitro-3,5,7-adamantanetriol and so on. Moreover, according to the present invention, oxidation of 1,3-dinitroadamantane with oxygen provides 1,3-dinitro-5-adamantanol, 1,3-dinitro-5,7-adamantanediol and so on.

The compound (Id) includes, for instance, 1-aminoadamantane, 1-amino-3-methyladamantane, 1-amino-3,5-dimethyladamantane, 1,3-diaminoadamantane, 1,3-diamino-5-methyladamantane, 1,3,5-triaminoadamantane. When the oxidation process with oxygen using the imide compound is applied to the compound (Id), an adamantane derivative in which $X^{2b}$ of the compound (Ia) is amino group [the compound having an amino group (Ia)] can be obtained. For example, when 1-aminoadamantane of the compound (Id) is subjected to the oxidation process by oxygen, 1-amino-3-adamantanol, 1-amino-3,5-adamantanediol, 1-amino-3,5,7-adamantanetriol and the like can be obtained. Moreover, oxidation of 1,3-diaminoadamantane by oxygen provides 1,3-diamino-5-adamantanol, 1,3-diamino-5,7-adamantanediol and so on. Oxidation of 1,3,5-triaminoadamantane provides 1,3,5-triamino-7-adamantanol and so on.

[Oxidation Catalyst]

An oxidation catalyst may comprise the imide compound (2) exemplified in the paragraphs of the nitration reaction, and may comprise the imide compound and a co-catalyst.

The co-catalyst includes metal compounds such as a compound comprising a Group 2A element of the Periodic Table (e.g., magnesium, calcium, strontium, barium), a transition metal compound, or a compound comprising a Group 3B element of the Periodic Table (e.g., boron B, aluminium Al). The co-catalyst may be employed singly or in combination of two or more.

As an element of the transition metal, there may be mentioned, for instance, a Group 3A element of the Periodic Table (e.g., a lanthanoid element such as lanthanum La, cerium Ce, samarium Sm, besides scandium Sc, yttrium Y; an actinoid element such as actinium Ac), a Group 4A element (e.g., titanium Ti, zirconium Zr, hafnium Hf), a Group 5A element (e.g., vanadium V, niobium Nb, tantalum Ta), a Group 6A element (e.g., chromium Cr. molybdenum Mo, tungsten W), a Group 7A element (e.g., manganese Mn, technetium Tc, rhenium Re), a Group 8 element (e.g., iron Fe, ruthenium Ru, osmium Os, cobalt Co, rhodium Rh, iridium Ir, nickel Ni, palladium Pd, platinum Pt), a Group 1B element (e.g., copper Cu, silver Ag, gold Au) and a Group 2B element of the Periodic Table (e.g., zinc Zn, cadmium Cd).

A preferred element constituting the co-catalyst includes an element of the transition metal (e.g., a Group 3A element such as a lanthanoid element, e.g., Ce, and an actinoid element; a Group 4A element such as Ti, Zr; a Group 5A element such as V, Nb; a Group 6A element such as Cr, Mo, W; a Group 7A element such as Mn, Tc, Re; a Group 8 element such as Fe, Ru, Co, Rh, Ni; and a Group 1B element of the Periodic Table such as Cu) and Group 3B elements of the Periodic Table such as B. The oxidation number of the metal element constituting the co-catalyst is not specifically limited and may be, for example, 0, +2, +3, +4, +5, or +6, depending on the species of the elements. As the co-catalyst, use may be practically made of a divalent transition metal compound (e.g., a divalent cobalt compound, a divalent manganese compound), a compound comprising a trivalent Group 5A element of the Periodic Table (e.g., a vanadium compound), a compound comprising a trivalent Group 6A element of the Periodic Table (e.g., a molybdenum compound) and the like.

The co-catalyst may be a simple substance or hydroxide of a metal. The co-catalyst may practically be an oxide of a metal (a double oxide or an oxygen acid or a salt thereof), an organic acid salt, an inorganic acid salt, a halide, each containing the element, a coordinate compound (a complex), a polyacid (in particular, a heteropolyacid or an isopolyacid) or its salt, each containing the metal element.

As the boron compound, there may be mentioned, for example, a boron hydroxide (e.g., borane, diborane, tetraborane, pentaborane, decaborane); aboric acid (e.g., orthoboric acid, metaboric acid , tetraboric acid); a borate (e.g., nickel borate, magnesium borate, manganese borate); a boron oxide such as $B_2O_3$; a nitrogen-containing boron compound such as borazane, borazene, borazine, boron amide, boron imide; a halide such as $BF_3$, $BCl_3$, tetrafluoroborate; an ester of boric acid (e.g., methyl borate, phenyl borate). A preferred boron compound includes boron hydrides, a boric acid and a salt thereof such as orthoboric acid (particularly a boric acid).

The hydroxide includes, for example, $Mn(OH)_2$, MnO(OH), $Fe(OH)_2$ and $Fe(OH)_3$. Examples of the metallic oxide include $Sm_2O_3$, $TiO_2$, $ZrO_2$, $V_2O_3$, $V_2O_5$, CrO, $Cr_2O_3$, $MoO_3$, MnO, $Mn_3O_4$, $Mn_2O_3$, $MnO_2$, $Mn_2O_7$, FeO, $Fe_2O_3$, $Fe_3O_4$, $RuO_2$, $RuO_4$, CoO, $CoO_2$, $Co_2O_3$, $RhO_2$, $Rh_2O_3$, $Cu_2O_3$, and so forth. As examples of the double oxide or oxygen acid salt, there may be mentioned $MnAl_2O_4$, $MnTiO_3$, $LaMnO_3$, $K_2Mn_2O_5$, $CaOxMnO_2$ (x=0.5, 1, 2, 3, 5), manganese salts [e.g., manganates(V) such as $Na_3MnO_4$, $Ba_3[MnO_4]_2$; manganates (VI) such as $K_2MnO_4$, $Na_2MnO_4$, $BaMnO_4$; permanganates such as $KMnO_4$, $NaMnO_4$, $LiMnO_4$, $NH_4MnO_4CsMnO_4$, $AgMnO_4$, $Ca(MnO_4)_2$, $Zn(MnO_4)_2$, $Ba(MnO_4)_2$, $Mg(MnO_4)_2$, $Cd(MnO_4)_2$].

As the organic acid salts, there may be exemplified salts with a $C_{2-20}$fatty acid such as cobalt acetate, manganese acetate, cobalt propionate, manganese propionate, cobalt naphthenate; manganese naphthenate, cobalt stearate, manganese stearate; manganese thiocyanate, and corresponding salts of Ce, Ti, Zr, V, Cr, Mo, Fe, Ru, Ni, Pd, Cu and Zn. As the inorganic acid salt, there may be mentioned, for instance, nitrates such as cobalt nitrate, iron nitrate, manganese nitrate, nickel nitrate, copper nitrate; and sulfates, phosphates and carbonates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned, for instance, chlorides such as $SmCl_3$, $SmI_2$, $TiCl_2$, $ZrCl_2$, $ZrOCl_2$, $VCl_3$, $VOCl_2$, $MnCl_2$, $MnCl_3$, $FeCl_2$, $FeCl_3$, $RuCl_3$, $CoCl_2$, $RhCl_2$, $RhCl_3$, $NiCl_2$, $PdCl_2$, $PtCl_2$, CuCl, $CuCl_2$; or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, CuBr, $CuBr_2$); a complex halide such as $M^1MnCl_3$, $M^1{}_2MnCl_4$, $M^1{}_2MnCl_5$, $M^1{}_2MnCl_6$, wherein $M^1$ represents a monovalent metal.

The ligand constituting the complex includes, for example, OH (hydroxo); an alkoxy group such as methoxy, ethoxy, propoxy, butoxy; an acyl group such as acetyl, propionyl; an alkoxycarbonyl group such as methoxycarbonyl (acetato), ethoxycarbonyl; acetylacetonato, cyclopentadienyl group; a halogen atom such as chlorine, bromine; CO; CN; oxygen atom; $H_2O$ (aquo); a phosphorus compound such as phosphine (e.g., triarylphosphine such as triphenylphosphine); a nitrogen-containing compound such as $NH_3$ (ammine), NO, $NO_2$ (nitro), $NO_3$ (nitrato), ethylenediamine, diethylenetriamine, pyridine, phenanthroline. In the complexes or complex salts, the same or different ligands may be coordinated singly or in combination of two or more.

The ligand is practically, for example, OH, an alkoxy group, an acyl group, an alkoxycarbonyl group, acetylacetonato, a halogen atom, CO, CN, $H_2O$ (aquo), phosphorus compound such as triphenylphosphine, or a nitrogen-containing compound inclusive of $NH_3$, $NO_2$ and $NO_3$.

The transition metal element and the ligand may be suitably employed in combination to form a complex. Such complex may be an acetylacetonato complex [e.g., an acetylacetonato complex of Ce, Sm, Ti, Zr, V, Cr, Mo, Mn, Fe, Ru, Co, Ni, Cu or Zn, titanylacetylacetonato complex $TiO(AA)_2$, zirconylacetylacetonato complex $ZrO(AA)_2$, vanadylacetylacetonato complex $VO(AA)_2$], a cyano complex [e.g., hexacyanomanganate(I), hexacyanoferrate(II)], a carbonyl complex or a cyclopentadienyl complex [e.g., tricarbonylcyclopentadienylmanganese(I), bixcyclopentadienylmanganese(II), biscyclopentadienyliron (II), $Fe(CO)_5$, $Fe_2(CO)_9$, $Fe_3(CO)_{12}$], a nitrosyl compound [e.g., $Fe(NO)_4$, $Fe(CO)_2(NO)_2$], a thiocyanato complex [e.g., thiocyanatoiron], or an acetyl complex [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$].

The polyacid is practically at least one member selected from Group 5A elements or Group 6A elements of the Periodic Table, such as V (vanadic acid), Mo (molybdic acid) or W (tungstic acid), typically speaking. There is no particular limit as to the central atom, and it may be any of, for instance, Be, B, Al, Si, Ge, Sn, Ti, Zr, Th, N, P, As, Sb, V, Nb, Ta, Cr, Mo, W, S, Se, Te, Mn, I, Fe, Co, Ni, Rh, Os, Ir, Pt, or Cu. As illustrative examples of the heteropolyacid, there may be mentioned cobaltmolybdic acid, cobalttungstic acid, molybdenumtungstic acid, manganesemolybdic acid, manganesetungstic acid, manganesemolybdenumtungstic acid, vanadomolybdophosphoric acid, manganesevanadiummolybdic acid, and manganesevanadomolybdophosphoric acid, vanadiummolybdic acid, vanadiumtungstic acid, silicomolybdic acid, silicotungstic acid, phosphomolybdic acid, phosphosungstic acid, phosphovanadomolybdic acid, and phosphovanadotungstic acid.

Among the co-catalysts mentioned above, the use of a divalent transition metal compound (e.g., a divalent cobalt compound, a divalent manganese compound) or a compound containing an element selected from a Group 4A element (e.g., Ti, Zr), a Group 5A element (e.g., V), a Group 6A element (e.g., Cr, Mo), a Group 7A element (e.g., Mn) and a Group 8 element (e.g., Co) of the Periodic Table enhances oxidation activity and provides an adamantane having a hydroxyl group with high conversion and selectivity. Specifically, the use of a compound containing a Group 5A element (e.g., V) as a co-catalyst insures efficient oxidation of plural positions of a substrate (e.g., a bridgehead position or a connecting position of adamantane) and provides an adamantane having plural hydroxyl groups introduced thereto.

Moreover, the use of a compound containing one element selected from a Group 4A element (e.g., Ti, Zr), a Group 5A) element (e.g., Cr, Mo) and a Group 7A element (e.g., Mn) of the Periodic Table inhibits deactivation of the catalyst (specifically the imide compound) even under severe conditions. Therefore, the substrate can be oxidized by oxygen with commercially advantageous efficiency.

The oxidation catalyst comprising the imide compound shown by the formula (2) or the imide compound and the co-catalyst may be whichever of a homogeneous system or a heterogeneous system. The catalyst may be a solid catalyst comprising a catalytic component supported on a support or carrier, as well. As the support or carrier, use can be made of the exemplified supports in the paragraphs of the nitration reaction. In the solid catalyst, the supported amount of the imide compound of the formula (2) as the catalyst component may be selected within the same range as the supported amount of the imide compound in the solid catalyst exemplified in the paragraphs of the nitration reaction. The supported amount of the co-catalyst is about 0.1 to 30 parts by weight, preferably about 0.5 to 25 parts by weight, and more preferably about 1 to 20 parts by weight, relative to 100 parts by weight of the support.

[Oxygen]

The oxygen utilized in the oxidation reaction may be whichever of pure oxygen or oxygen diluted with an inert gas (e.g., carbon dioxide, nitrogen, helium or argon gas). Moreover, air may be employed as an oxygen source.

The amount of the imide compound shown by the formula (2) may be selected from the ranges exemplified in the paragraphs of the nitration reaction as to the amount of the imide compound.

The amount of the co-catalyst may be selected within a wide range such as about 0.0001 mole (0.01 mole %) to 0.7 mole (70 mole %), preferably about 0.0001 to 0.5 mole, more preferably about 0.001 to 0.3 mole, and practically about 0.0005 to 0.1 mole (e.g., 0.005 to 0.1 mole) relative to 1 mole of the substrate.

The ratio of the co-catalyst to the imide compound shown by the formula (2) may be selected within a range not interfering with the reaction rate or selectivity, for example, of about 0.001 to 10 mole, preferably about 0.005 to 5 mole, more preferably about 0.01 to 3 mole, and may be practically about 0.01 to 5 mole (particularly 0.001 to 1 mole) of the co-catalyst, relative to 1 mole of the imide compound.

Activity of the imide compound sometimes deteriorates as the amount of the co-catalyst increases. Therefore, in order to maintain the high activity of the oxidation catalyst system, the ratio of the co-catalyst is preferably in a range of an effective amount and about 0.1 mole (e.g., about 0.001 to 0.1 mole, preferably about 0.005 to 0.08 mole, more preferably about 0.01 to 0.07 mole) relative to 1 mole of the imide compound.

The amount of oxygen may be selected according to the species of the substrate, and the range may practically be about 0.5 mole or more (e.g., 1 mole or more), preferably about 1 to 100 mole, more preferably about 2 to 50 mole, relative to 1 mole of the substrate. Excess amount of oxygen relative to a substrate may practically be employed. Specifically, the reaction under an atmosphere containing molecular oxygen such as air or oxygen is advantageous.

The oxidation reaction may be conducted in an organic solvent inert to the reaction. As the organic solvent, use can be made of the organic solvents exemplified in the paragraphs of the nitration reaction. Preferred organic solvents include organic acids (e.g., carboxylic aids such as acetic acid), nitrites (e.g., benzonitrile) and the like.

In the present invention, the oxidation reaction with oxygen can be smoothly conducted even under comparatively mild or moderate conditions. The reaction temperature may be selected, according to species of the imide compound or the substrate, within a range of about 0 to 300° C., preferably about 10 to 250° C. (e.g., 10 to 200° C.), more preferably about 10 to 150° C., and practically about 10 to 100° C. (e.g., 10 to 80° C.). The reaction can be conducted at ambient pressure (atmospheric pressure) or under a pressure (under a load).

[Reduction Reaction]

In the reaction step scheme (I), the reduction reaction which produces the compound (Ia) or (Id) each having an amino group by reducing the compound (Ic) or (Ie) having a nitro group, can be conducted by a conventional process such as the catalytic hydrogenation process using hydrogen as a reducing agent and a reduction process using a hydrogenation reducing agent.

In the catalytic hydrogenation, a simple substance of a metal such as platinum, palladium, nickel, cobalt, iron and copper, a compound containing such metal elements (e.g., platinum oxide, palladium black, palladium carbon and copper chromite) or the like may be used as a catalyst. The amount of the catalyst is practically about 0.02 to 1 mole relative to 1 mole of a substrate. Further, in a catalytic hydrogenation, the reaction temperature may be, for example, about −20 to 100° C. (e.g., about 0 to 90° C.). A hydrogen pressure is practically about 1 to 100 atm (e.g., about 1 to 50 atm).

In the reduction process using a hydrogenation reducing agent, as the hydrogenation reducing agent to be used, there may be mentioned, for example, aluminium hydride, lithium aluminium hydride, lithium trialkoxyaluminium hydride, sodium boron hydride, diborane, bis-3-methyl-2-butylborane, a metal (e.g., zinc, tin, iron) acid, a sulfide and hydrazine. The reducing process using a hydrogenation reducing agent may be conducted also in the presence of a Lewis acid such as aluminium chloride anhydride and boron trifluoride. The amount of the hydrogenation reducing agent is practically about 1 mole or more (e.g., about 1 to 10 mole) relative to 1 mole of a substrate. In the reduction process using the hydrogenation reducing agent, the reaction temperature is practically about 0 to 200° C. (e.g., about 0 to 170° C.).

Incidentally, the reduction reaction (the catalytic hydrogenation process and the reaction by the process using the hydrogenation reducing agent) may be carried out in the presence of a solvent inert to the reduction reaction (e.g., an alcohol such as methanol; a solvent exemplified in the paragraphs of the nitration reaction, such as a carboxylic acid, an ether, an ester and an amide). Moreover, when the reduction reaction is conducted by the catalytic hydrogenation process, an acid such as hydrochloric acid may be added to the reaction system in order to improve the catalytic activity.

Reduction of the compound (Ic) provides the compound (Id), for example, reduction of 1-nitroadamantane of the compound (Ic) provides 1-aminoadamantane.

The compound (If) corresponds to a compound in which $X^{2b}$ of the compound (Ia) is nitro group. Reduction of the compound (If) provides a compound in which $X^{2b}$ is amino group. For example, reduction of 1-nitro-3,5-adamantanediol of the compound (If) provides 1-amino-3,5-adamantanediol, and reduction of 1-nitro-3-adamantanol provides 1-amino-3-adamantanol.

According to the species of substrate, hydroxyl group [e.g., hydroxyl group of the compound (Ia), the compound (Ie) or the compound (If)], hydroxylmethyl group (a moiety corresponding to hydroxyl group of hydroxymethyl group), amino group [e.g., amino group of the compound (Ia) or the compound (Id)] or carboxyl group of the reaction component or the reaction product may be optionally protected by the protecting group before or after the nitration reaction, oxidation reaction or the reduction reaction, or during each reaction steps. Introduction and elimination of the protecting group for hydroxyl group, hydroxymethyl group, amino group and carboxyl group may be carried out by utilizing a conventional method such as esterification, amidation, carbamation, carbonation, hydrolysis and hydrogenolysis, if necessary, using an acid, an alkali, an ion-exchange resin, a catalyst for hydrogenolysis or the like.

When an acyl group is used as a protecting group for hydroxyl group or amino group, hydroxyl group or amino group of the substrate may be protected by allowing an acylating agent to act on the substrate. As the acylating agent, there may be exemplified $C_{2-6}$ aliphatic monocarboxylic acids such as acetic acid, propionic acid, n-butyric acid, isobutyric acid, valeric acid and pivalic acid (preferably $C_{2-4}$ carboxylic acids), and reactive derivatives thereof [e.g., acid anhydrides such as acetic anhydride and valeic anhydride, acid halides such as acid chloride (e.g., acetyl chloride, propionyl chloride and butyryl chloride)]. When an acid anhydride or an acid halide is used as an acylating agent, the reaction is practically carried out in the presence of a base in order to capture the acid which is a by-product in the reaction. As the base, there may be mentioned, for example, an inorganic base (e.g., a hydroxide of an alkali metal such as sodium hydroxide; a hydroxide of alkaline earth metal such as barium hydroxide; carbonate of an alkaline metal such as sodium carbonate; a carbonate of an alkaline earth metal such as barium carbonate; a hydrogencarbonate of an alkaline metal such as sodium hydrogencarbonate); and an organic base (e.g., a tertiary amine such as triethylamine and N-methylpiperidine; a basic heterocyclic compound containing a nitrogen atom such as pyridine. The acylating agent may be used singly or in combination of two or more.

Reaction of 1-nitro-3-adamantanol of the compound having a hydroxyl group [e.g., the compound (Ia), the compound (If)] with acetic acid (or acetyl chloride or acetic anhydride) provides 1-nitro-3-acetyloxyadamantane. Moreover, 1-acetyloxy-3-aminoadamantane can be obtained by reducing the 1-nitro-3-acetyloxyadamantane. Similarly, 1-acetyloxy-3-adamantanol and/or 1,3-bis(acetyloxy) adamantane from 1,3-adamantanediol; 1-acetylamino-3-adamantanol and/or 1-acetylamino-3-acetyloxyadamantane from 1-amino-3-adamantanol; 1-acetyloxy-3-carboxyadamantane from 1-carboxy-3-adamantanol; 1-acetyloxy-3-methoxycarbonyladamantane from 1-methoxycarbonyl-3-adamantanol; 1-acetyloxy-3-hydroxymethyladamantane and/or 1-acetyloxymethyl-3-adamantanol and/or 1-acetyloxy-3-acetyloxymethyladamantane from 1-hydromethyl-3-adamantanol; and 1-acetyloxy-3,5-adamantanediol and/or 1,3-bis(acetyloxy)-5-adamantanol and/or 1,3,5-tris (acetyloxy)adamantane from 1,3,5-adamantanetriol can be obtained.

1-acetylamino-3-adamantanol, 1-acetylamino-3,5-adamantanediol, 1-acetylamino-3,5,7-adamantanetriol and the like are obtained by reacting 1-aminoadamantane of the compound having an amino group (Id) with acetic acid to oxidize with oxygen.

In the oxidation by oxygen, the use of a carboxylic acid (e.g., a carboxylic acid such as acetic acid, propionic acid) as a solvent insures protection of hydroxyl group and amino group by a protective group (e.g., an acyl group) in the process of the oxidation reaction.

When carbonate group is used as a protected hydroxyl group or when carbamate group is used as a protected amino group, for example, a halogenated carboxylic acid ester may be allowed to react with a compound having a hydroxyl group or a compound having an amino group to convert the hydroxyl group or the amino group into each corresponding carbonate group or carbamate group. This reaction is practically carried out in the presence of a base. As the base, use can be made of the above exemplified bases.

For example, 1-methoxycarbonyloxy-3-adamantanol and/or 1,3-bis(methoxycarbonyloxy)adamantane can be obtained by allowing chloromethoxycarbonyl (methyl chlorocarbonate) to react with 1,3-adamantanediol. Similarly, 1-carboxy-3-methoxycarbonyloxyadamantane from 1-carboxy-3-adamantanol; 1-methoxycarbonyl-3-methoxycarbonyloxyadamantane from 1-methoxycarbonyl-3-adamantanol; 1-acetyloxy-3-methoxycarbonyloxyadamantane from 1-acetyloxy-3-adamantanol; 1-acetylamino-3-methoxycarbonyloxyadamantane from 1-acetylamino-3-adamantanol; 1-hydroxymethyl-3-methoxycarbonyloxyadamantane and/or 1-methoxycarbonyloxymethyl-3-adamantanol and/or 1-methoxycarbonyloxy-3-methoxycarbonyloxymethyladamantane from 1-hydroxymethyl-3-adamantanol; 1-(N,N-dimethylcarbamoyl)-3-methoxycarbonyloxydadamantane from 1-(N,N-dimethylcarbamoyl)-3-adamantanol; 1-(methoxycarbonyloxy)-3-nitroadamantane from 1-nitro-3-adamatanol; 1-(methoxycarbonyloxy)-3,5-adamantanediol and/or 1,3-bis(methoxycarbonyloxy)-5-adamantanol and/or 1,3,5-tris(methoxycarbonyloxy) adamantane from 1,3,5-adamantanetriol; 1,3-bis (methoxycarbonyloxy)-5-nitroadamantane from 1-nitro-3,5-adamantanediol; and 1-carboxy-3,5-bis (methoxycarbonyloxy)adamantane from 1-carboxy-3,5-adamantanediol can be obtained.

When carbamoyloxy group is used as a protected hydroxyl group, for example, an isocyanate compound may be allowed to react with a compound having a hydroxyl group, if necessary, in the presence of the above exemplified base or the like to convert the hydroxyl group into the corresponding carbamoyloxy group. For example, in the presence of pyridine, methyl isocyanate may be allowed to react with 1,3-adamantanediol to form 1-(N-methylcarbamoyloxy)-3-adamantanol and/or 1,3-bis(N-methylcarbamoyloxy)adamantane. Similarly, 1-(N-methylcarbamoyloxy)-3,5-adamantanediol and/or 1,3-bis (N-methylcarbamoyloxy)-5-adamantanol and/or 1,3,5-tris (N-methylcarbamoyloxy)adamantane can be obtained from 1,3,5-adamantanetriol.

Moreover, an adamantane derivative having an N-substituted amino group and a hydroxyl group can be obtained, for example, (i) by reacting the compound (Ia) having an amino group with a hydrocarbon halide (e.g., aliphatic hydrocarbon halide such as iodomethane, iodoethane, iodobutane, bromomethane, bromoethane, bromobutane, chloromethane and chloroethane) or (ii) by subjecting a compound produced by the reaction of the compound (Id) with a hydrocarbon halide, that is, a compound in which an amino group of the compound (Id) is converted into an N-substituted amino group, to the oxidation reaction by oxygen with the use of the imide compound (2). The reaction of the compound (Ia) or the compound (Id) having an amino group with a hydrocarbon halide may be carried out in the presence of a de-hydrogen halide agent (an agent for eliminating a hydrogen halide). As the de-hydrogen halide agent, use can be practically made of a basic compound [for example, an organic base (e.g., a basic nitrogen-containing compound such as an aliphatic amine e.g., trimethylamine, triethylamine, dimethylamine, diethylamine, methylenediamine and ethylenediamine; a heterocyclic amine e.g., pyridine and morpholine), an inorganic base (e.g., a hydroxide of an alkali metal such as sodium hydroxide and potassium hydroxide; a hydroxide of alkaline earth metal such as calcium hydroxide; a carbonate of alkali metal such as sodium carbonate and potassium carbonate; a carbonate of an alkaline earth metal such as calcium carbonate; a hydrogencarbonate of an alkali metal such as sodium bicarbonate and potassium bicarbonate; an alkoxide of an alkali metal such as sodium methoxide and sodium ethoxide)].

The reaction of the compound (Ia) or the compound (Id) each having an amino group with a hydrocarbon halide may be conducted in a solvent inert to the reaction. As such solvent, use may be made of the solvents exemplified in the paragraphs of the nitration reaction, such as a hydrocarbon halide, an ether, an ester and an amide.

Reaction of 1,3-diamino-5-adamantanol with iodomethane provides 1,3-di(methylamino)-5-adamantanol, 1,3-di(dimethylamino)-5-adamantanol, etc. Reaction of 1,3-diamino-5,7-adamantanediol with iodoethane provides 1,3-di(ethylamino)-5,7-adamantanediol, 1,3-di(diethylamino)-5,7-adamantanediol, etc.

When a carboxyl group is protected by an alkoxy group (when an ester group is formed), the carboxyl group may be converted into the corresponding ester group by reacting a carboxyl group-containing compound or a derivative thereof (e.g., an acid halide such as an acid chloride) with an alcohol (e.g., methanol, ethanol) or a reactive derivative thereof (e.g., a lower alkyl ester), if necessary, in the presence of an acid (e.g., a mineral acid such as hydrochloric acid and sulfuric acid) or a base (e.g., the above exemplified base). The lower alkyl ester includes, for example, acetic acid $C_{1-4}$alkyl ester such as methyl acetate and ethyl acetate or the corresponding propionate (e.g., methyl propionate, ethyl propionate). For example, 1-methoxycarbonyl-3-adamantanol may be obtained by reacting 1-carboxy-3-adamantanol with methanol in the presence of an acid, or by acting thionyl chloride on 1-carboxy-3-adamantanol followed by reacting with methanol in the presence of an organic base such as triethylamine.

Moreover, when a carboxyl group is converted into a group having an amide bond, with the use of an amino group as a protecting group for the carboxyl group (i.e., when forming an N-substituted or unsubstituted carbamoyl group), conditions of a conventional process for forming an amide bond may be applied. The process for forming an amide bond may be carried out, for example, by the following methods:

(a) a method by a mixed acid anhydride, i.e., a method which comprises reacting a compound having a carboxyl group with an acid halide (e.g., acetyl chloride, propionyl chloride, acetyl bromide) to produce a mixed acid anhydride followed by reacting the given mixed acid anhydride with an amine compound;

(b) a method by an active ester, i.e., a method which comprises converting a substrate into an active ester thereof, such as p-nitrophenylester, an ester with N-hydroxysuccinimide, an ester with 1-hydroxybenzotriazol or the like followed by reacting the given ester with an amine compound;

(c) a method by a carbodiimide, i.e., a method which condenses an amine compound with a substrate in the presence of an activating agent such as dicyclohexylcarbodiimide and carbonyldiimidazol; or (d) a method which comprises converting a substrate into a carboxylic anhydride thereof by a dehydrator such as acetic anhydride followed by reacting the given carboxylic anhydride with an amine compound, or a method which comprises converting a substrate to an acid halide thereof followed by reacting the acid halide with an amine compound.

The amine compound used in the amide bond-forming reaction includes, for example, ammonia or a derivative thereof (e.g., ammonium halide such as ammonium chloride), a primary amine, a secondary amine, hydrazine or a derivative thereof (e.g., alkoxycarbonylhydrazine such as t-butoxycarbonylhydrazine, alkoxycarbonylhydrazine such as benzyloxycarbonylhydrazine).

For example, the reaction of an acid halide with an amine compound may be carried out in a suitable solvent, in the presence of an basic compound. As the basic compound, use may be made of the basic compounds exemplified in the paragraphs of the reaction of the compound (Ia) having an amino group or the compound (Id) with a hydrocarbon halide and the like.

Moreover, as the solvent, an organic solvent (e.g., an ether, an ester, an amide) exemplified f or the nitration reaction may be employed.

For example, reaction of 1,3-dicarboxy-5-adamantanol with ammonia provides 1,3-dicarbamoyl-5-admatanol. Reaction of 1,3-dicarboxy-5,7-adamantanediol with hydrazine forms 1,3-di(hydrazinocarbonyl)-5,7-adamantanediol, etc. 1-(N,N-dimethylcarbamoyl)-3-adamantanol can be obtained by acting thyonyl chloride on 1-carboxy-3-adamantanol followed by reacting the resultant compound with dimethylamine. Similarly, 1-(N,N-dimethylcarbamoyl)-3-methoxycarbonyladamantane can be formed from 1-carboxy-3-methoxycarbonyladamantane, Furthermore, the compound having a carbamoyl group may also be obtained by reacting a compound having an ester group (e.g., an alkoxycarbonyl group, an aryloxycarbonyl group, an aralkylcarbonyl group) as a protected carboxyl group with the amine compound in the presence of a catalyst comprising a metal compound.

Examples of the metal compound used in the reaction (the amidation reaction) include a conventional catalyst for transesterification (including a catalyst for transferring an ester to an amide), for example, a transition metal compound such as a compound comprising Group 3B element of the Periodic Table (e.g., aluminum compound such as $AlCl_3$), a compound comprising Group 4A element of the Periodic Table (e.g., titanium compound such as $TiCl_4$), a compound comprising Group 3A element (e.g., samarium compound such as $SmI_2$) of the Periodic Table.

The amount of the catalyst may be selected within a broad range, for example, about 0.1 mole % to 1 equivalent, preferably about 0.5 to 50 mole %, and more preferably about 1 to 25 mole % (e.g., about 5 to 20 mole %) relative to a compound having an ester group.

The ratio of the amine compound to the ester group-containing compound is, for example, about 0.5 to 5 mole, preferably about 0.8 mole or more (e.g., about 0.8 to 5 mole), and specifically about 1 mole or more (e.g., about 1 to 3 mole, in particular about 1 to 1.5 mole) of ammonia or the like relative to 1 equivalent of the ester group-containing compound.

The amidation reaction may be carried out in the presence or absence of a solvent inert to the reaction. As the reaction solvent, there may be exemplified an aliphatic hydrocarbon, an alicyclic hydrocarbon, an aromatic hydrocarbon, a ketone, an ether, a non-protonic polar solvent and a mixture thereof. The reaction temperature may be selected within the range of, for example, about 0 to 150° C., and preferably about 25 to 120° C.

An adamantane derivative having plural hydroxyl groups (containing a hydroxyl group protected by a protective group) can be obtained according to the following reaction step scheme (II).

Reaction step scheme (II)

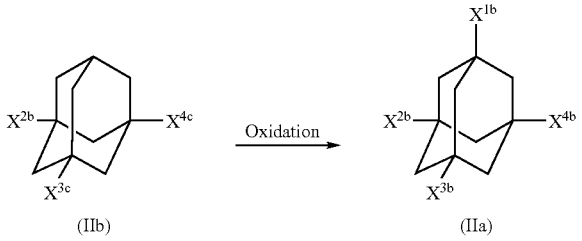

Wherein $X^{2b}$ and $X^{21}$ represent H or OH, $X^{3h}$ and $X^{4h}$ may be the same or different and each may represent H, R, $NO_2$, OH, $NH_2$, COOH, $CH_2OH$ or NCO. $X^{1b}$, $X^{3c}$ and $X^{4c}$ have the same meanings as defined above.

In the reaction step scheme (II), the oxidation reaction which leads the compound (IIb) to the compound (IIc) may be carried out by the oxidation reaction (the oxidation reaction with oxygen) using an oxidation catalyst comprising the imide compound (2). For example, oxidation of 1-adamantanol forms 1,3-adamantanediol, 1,3,5-adamantanetriol, etc. Oxidation of 1,3-adamantanediol provides 1,3,5-adamantanetriol, etc.

Incidentally, according to the species of substrate, hydroxyl group, hydroxymethyl group, amino group and carboxyl group of the reaction component or the reaction product may be protected by the above protecting group before, after, or during the oxidation reaction. The introduction and elimination of the protecting group may be carried out by a method similar to the above described method.

Specifically, an group derivative having a non-polymerizable acyloxy group among the group derivatives having plural hydroxyl groups (including a hydroxyl group protected by a protective group) can be obtained in accordance with the following reaction step scheme (II-1).

Reaction step scheme (II-1)

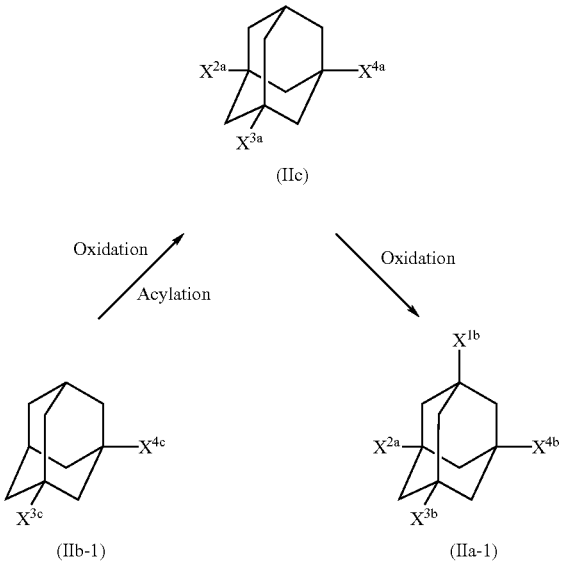

Wherein $X^{3i}$ and $X^{4i}$ may be the same or different and each may represent H, R, $NO_2$, OH, $NH_2$, COOH, $CH_2OH$ or NCO, and $X^{2r}$ represents OAc, $X^{1b}$, $X^{3c}$, $X^{4c}$, $X^{3h}$ and $X^{4h}$ have the same meanings as defined above.

In the reaction step scheme (II-1), the oxidation reaction which leads the compound (II-1) to (IIc) and the oxidation reaction which forms the compound (IIa-1) from the compound (IIc) can be carried out by the above mentioned oxidation process by oxygen. Moreover, acylation may be carried out by reacting a substrate with the acylating agent. The acylation may be conducted before, after or during the oxidation reaction.

The compound (IIb-1) corresponds to the compound (Ib). The compound (IIb-1) may be oxidized and reacted with an acylating agent to produce the compound (IIc). For example, 1-acetyloxyadamantane, 1,3-acetyloxyadamantane, 1,3,5-acetyloxyadamantane or the like can be obtained by subjecting adamantane of the compound (IIb-1) to the oxidation by oxygen with the aid of the imide compound (2) and reacting the resultant compound with acetic acid.

The comopound (IIc) includes, for example, an adamantane having a $C_{2-6}$acyl-oxy group such as 1-acetyloxyadamantane, 1-acetyloxy-3-methyladamantane, 1-acetyloxy-3,5-dimethyladamantane, 1,3-diacetyloxyadamantane, 1,3-diacetyloxy-5-methyladamantane, 1,3,5-triacetyloxyadamantane. The oxidation process with oxygen may be applied to the compound (IIc) to produce the compound (IIa-1). 1-acetyloxyadamantane of the compound (IIc) maybe subjected to the oxidation process by oxygen using the imide compound (2) to produce 1-acetyloxy-3-adamantanol, 1-acetyloxy-3,5-adamantandiol, 1-acetyloxy-3,5,7-adamantanetriol, etc. Further, according to the present invention, 1,3-diacetyloxy-5-adamantanol and 1,3-diacetyloxy-5,7-adamantanediol can be obtained by the oxidation of 1,3-diacetyloxyadamantane with oxygen. 1,3,5-triacetyloxy-7-adamantanol can be obtained by applying the oxidation process with oxygen to 1,3,5-triacetyloxyadamantane.

The compound (IIa-1) may be obtained also be oxidizing the compound (IIb-1) with oxygen to form an adamantane derivative having at least two hydroxyl groups (e.g., 1,3-adamantanediol, 5-methyl-1,3-adamantanediol, 5,7-dimethyl-1,3-adamantanediol, 1,3,5-adamantanetriol and 1,3,5,7-adamantanetetraol) followed by acting an acylating agent.

An adamantane derivative having a carboxyl group (containing a carboxyl group protected by a protective group) together with a hydroxyl group (containing a hydroxyl group protected by a protective group) can be obtained in accordance with, for example, the following reaction step scheme (III).

Reaction step scheme (III)

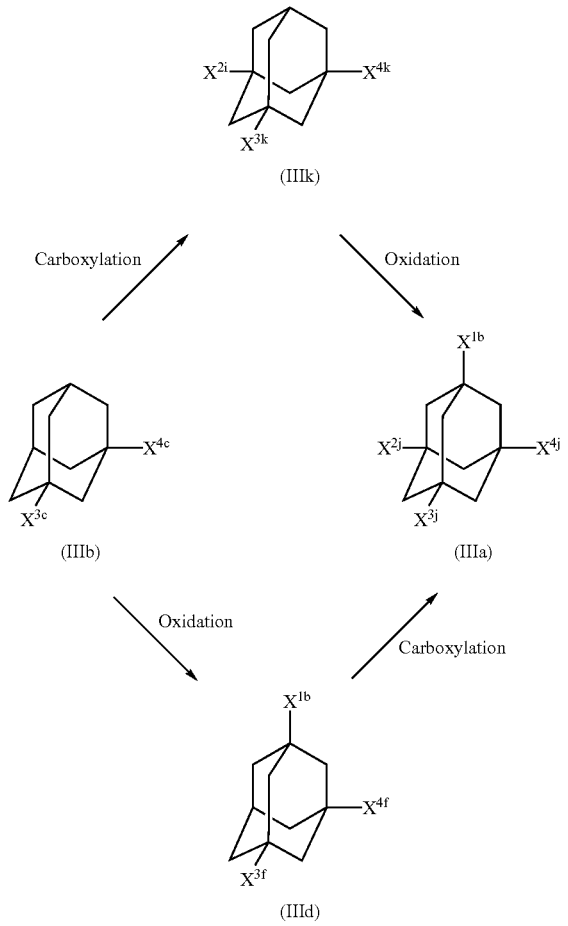

Where $X^{2j}$ represents COOH and $X^{3j}$, $X^{4j}$, $X^{3k}$ and $X^{4k}$ may be the same or different and each may represent H, R, $NO_2$, OH, $NH_2$, COOH, $CH_2OH$ and NCO. $X^{1b}$, $X^{3e}$, $X^{4e}$, $X^{3f}$ and $X^{4f}$ have the same meanings as defined above.

In the reaction step scheme (III), the oxidation. reaction which leads the compound (IIb) to the compound (IIId) and the oxidation reaction which forms the compound (IIIa) from the compound (IIIc) can be carried out by the oxidation reaction (the oxidation reaction with oxygen) using an oxidation catalyst comprising the imide compound (2) or a catalyst system comprising the inside compound (2) and a co-catalyst.

The compound (IIIb) corresponds to the compound (Ib), and oxidation of the compound (IIIb) with oxygen provides the compound (IIId), that is, the compound (Ie).

The compound (IIIc) includes, for example, 1-carboxyadamantane, 1-carboxy-3-methyladamantane, 1-carboxy-3,5-dimethyladamantane, 1,3-dicarboxyadamantane, 1,3-dicarboxy-5-methyladamantane, 1,3,5-tricarboxyadamantane. The compound (IIIa) can be proposed by oxidizing the compound (IIIc) by oxygen with the aid of an oxidation catalyst comprising the imide compound. (2) in a manner similar to that of the oxidation reaction. The oxidation process by oxygen with aid of the imide compound (2) may be applied to 1-carboxyadamantane of the compound (IIIc) to provide 1-carboxy-3-adamantanol, 1-carboxy-3,5-adamantandiol, 1-carboxy-3,5,7-adamantanetriol, etc. Oxidation of 1,3-dicarboxyadamantane with oxygen provides 1,3-dicarboxy-5-adamantanol, 1,3-dicarboxy-5,7-adamantanediol, etc. Oxidation of 1,3,5-tricarboxyadamantane with oxygen provides 1,3,5-tricarboxy-7-adamantanol.

[Carboxylation Reaction]

In the reaction step scheme (III), to the carboxylation reaction which forms the compound (IIIc) from the compound (IIIb) and the carboxylation reaction which leads the compound (IIId) to the compound (IIIa) may be applied a process comprising contacting the substrate [the compound (IIIb), the compound (IIId)] with carbon monoide and oxygen in the presence of a catalyst comprising the imide compound shown by the formula (2).

The compound (IIIb) may be subjected to the carboxylation reaction to provide the compound (IIIc). Adamantane of the compound (IIIb) may be subjected to the carboxylation reaction to provide 1-carboxyadamantane, 1,3-dicarboxyadamantane, 1,3,5-tricarboxyadamantane, etc. Carboxylation of 1,3-adamantanediol provides 1-carboxy-3,5-adamantadiol, etc.

Moreover, the compound (IIId) may be subjected to the carboxylation reaction (the carboxylation process) using the imide compound (2) to provide the compound (IIIa). 1-adamantanol of the compound (IIId) may be subjected to the carboxylation reaction using the imide compound (2) to produce 1-carboxy-3-adamantanol, 1,3-dicarboxy-5-adamantanol, 1,3,5-tricarboxy-7-adamantanol, etc.

[Catalyst]

As an imide compound in the carboxylation reaction, use can be made of the imide compound (2) exemplified in the paragraphs of the nitration reaction. In this carboxylation reaction, a catalyst may comprise an imide compound (2) similar to that used in the oxidation reaction and a co-catalyst.

[Carbon Monoxide and Oxygen]

Carbon monoxide to be used in the carboxylation reaction may be pure carbon monoxide or diluted with an inert gas exemplified in the paragraphs of oxygen for the oxidation reaction. Oxygen may be one of those exemplified in the paragraphs of the oxidation reaction.

In the carboxylation reaction, the amount of the imide compound shown by the formula (2) may be selected within the range of the amount of the imide compound exemplified in the paragraphs of the nitration reaction using the inside compound (2).

The amount of the co-catalyst may be selected within the range of the amount of the co-catalyst exemplified in the paragraphs of the oxidation reaction with oxygen using the imide compound (2). Similarly, the ratio of the co-catalyst to the imide compound may be selected within the range of the ratio of the co-catalyst to the imide compound exemplified in the paragraphs of the oxidation reaction with oxygen.

The amount of carbon monoxide may be selected within a range of, for example, about 1 mole or more (e.g., about 1 to 1000 mole), preferably excess mole, for example, about 1.5 to 100 mole (e.g., about 2 to 50 mole), more preferably about 2 to 30 mole (e.g., about 5 to 25 mole), relative to 1 mole of the substrate.

The amount of oxygen may be selected within a range of about 0.5 mole or more (e.g., about 0.5 to 100 mole), preferably about 0.5 to 30 mole, more preferably about 0.5 to 25 mole, relative to 1 mole of the substrate.

The ratio of carbon monoxide (CO) to oxygen ($O_2$) may be selected within a wide range, as far as the amount of each component is within the above range, for example, of $CO/O_2$=about 1/99 to 99.99/0.01 (mole %). The use of the carbon monoxide in the amount larger than that of oxygen is advantageous. The ratio of CO to $O_2$ may be usually selected within the range of $CO/O_2$=about 1/99 to 99/1 (mole %) [e.g., about 10/90 to 99/1 (mole %)], and preferably about 30/70 to 98/2 (mole %), more preferably about 50/50 to 95/5 (mole %), particularly about 60/40 to 90/10 (mole %).

The volume ratio of carbon monoxide to oxygen in a supply line may be selected within the range of, for example, $CO/O_2$=about 1/99 to 99.99/0.01 (volume %), and usually about 1/99 to 99/1 (volume %), preferably about 30/70 to 98/2 (volume %), more preferably about 50/50 to 95/5 (volume %), specifically about 60/40 to 90/10 (volume %).

The carboxylation reaction may be conducted in an organic solvent inert to the reaction. As the organic solvent, use can be made of the organic solvents exemplified in the paragraphs of the nitration reaction, and practically an organic acid (e.g., a carboxylic acid such as acetic acid), a nitrile (e.g., acetonitrile), a hydrocarbon halide (e.g., dichloroethane).

The carboxylation reaction using the imide compound (2) can be smoothly conducted even under comparatively mild or moderate conditions. The reaction temperature may be selected, according to species of the imide compound or the substrate, within the range of about 0 to 200° C., preferably about 10 to 150° C. (e.g., about 10 to 120° C.), more preferably about 10 to 100° C. (e.g., about 10 to 80° C.). The reaction can be conducted at ambient pressure or under a pressure (under a load).

According to species of the substrate, hydroxyl group [e.g., hydroxyl group of the compound (IIIa) and the compound (IIId)], hydroxymethyl group, amino group and carboxyl group [e.g., carboxyl group of the compound (IIIa) and the compound (IIIc)] of the reaction component or the reaction product may be protected by the above protecting group before or after the oxidation reaction or the carboxylation reaction, or during each reaction. Introduction and elimination of these protecting groups may be carried out by a method similar to the above described method.

For example, 1-carboxy-3-acetyloxyadamantane, 1-carboxy-3,5-diacetyloxyadamantane, 1-carboxy-3,5,7-triacetyloxyadamantane or the like can be obtained by oxidizing 1-carboxyadamantane of the compound (IIIc) and reacting the produced alcohol bodies with acetic acid. Similarly, reaction of 1-carboxy-3-adamantanol of the compound (IIIa) with methanol provides 1-methoxycarbonyl-3-adamantanol. 1-carboxyadamantane of the compound (IIIc) may be allowed to react with ethanol and subjected the oxidation reaction with oxygen to produce 1-ethoxycarbonyl-3-adamantanol, 1-ethoxycarbonyl-3,5-adamantanediol, 1-ethoxycarbonyl-3,5,7-adamantanetriol, etc. 1,3-dicarboxyadamantane may be allowed to react with ethanol and oxidized with oxygen to produce 1,3-di(ethoxycarbonyl)-5-adamantanol, 1,3-di(ethoxycarbonyl)-5,7-adamantanediol, etc.

When an alcohol or a lower alkyl ester thereof (e.g., ethyl acetate) is used as a solvent and a substrate subjected to the carboxylation reaction, an adamantane derivative having a carboxyl group protected by a protective group (an alkoxy group) can be obtained.

An adamantane derivative having a hydroxymethyl group (containing a hydroxymethyl group protected by a protective group) together with a hydroxyl group (containing a hydroxyl group protected by a protective group) can be obtained in accordance with the following reaction step scheme (IV).

Reaction step scheme (IV)

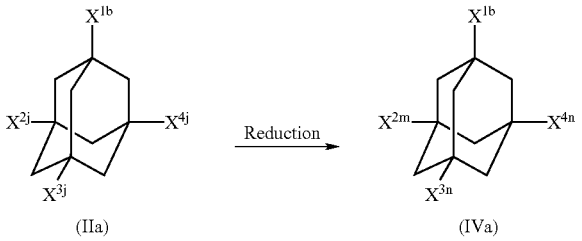

Wherein $X^{2m}$ represents $CH_2OH$, $X^{3n}$ and $X^{4n}$ may be the same or different and each may represent H, R, $NO_2$, OH, $NH_2$, $CH_2OH$ and NCO. $X^{1b}$, $X^{2f}$, $X^{3f}$ and $X^{4j}$ have the same meanings as defined above.

In the reaction step scheme (IV), the reduction reaction which leads the compound (IIIa) to the compound (IVa) may be carried out by a conventional method such as a catalytic hydrogenation process using hydrogen as a reducing agent and a reduction process using a hydrogenation reducing agent. Preferred hydrogenation reducing agent includes, for example, sodium boron hydride-Lewis acid, aluminium hydride, lithium aluminium hydride, lithium trialkoxyaluminium hydride and diborane. Incidentally, the compound (IIIa) can be obtained by the reaction step scheme (III).

For example, 1-hydroxy-3-hydroxymethyladamantane can be formed by reducing 1-carboxy-3-adamantanol with lithium aluminium hydride.

According to the species of the substrate, hydroxyl group, hydroxymethyl group, amino group and carboxyl group of the reaction component or the reaction product may be protected by the above protecting group before or after the reduction reaction. Introduction and elimination of these protecting groups may be carried out by a method similar to the above described method.

An adamantane derivative having an isocyanato group together with a hydroxyl group (containing a hydroyl group protected by a protective group) can be obtained, for example, in accordance with the following reaction step scheme (V).

Reaction step scheme (V)

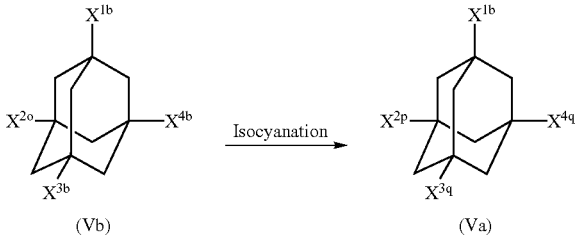

Wherein $X^{2o}$ represents $NH_2$, $X^{2p}$ represents NCO, and $X^{3q}$ and $X^{4q}$ may be the same or different and each may represent H, R, $NO_2$, OH, $NH_2$, COOH, $CH_2OH$ and NCO. $X^{1b}$, $X^{3b}$ and $X^{4b}$ have the same meanings as defined above.

In the reaction scheme (V), the reaction which leads the compound (Vb) to the compound (Va) may be conducted by a conventional method such as a method using phosgene. The compound (Vb) corresponds to a compound in which $X^{2b}$ of the compound (Ia) obtained in the reaction step scheme (I) is $NH_2$.

The reaction of the compound (Vb) with phosgene may be conducted, for example, in the presence or absence of a solvent at a temperature of about −10 to 100° C. The amount of phosgene is, for example, about 0.8 to 10 mole and preferably about 1 to 2 mole relative to 1 mole of the compound (Vb).

For example, 1-acetyloxy-3-isocyanatoadamantane can be obtained by allowing 1-acetyloxy-3-aminoadamantane to react with phosgene.

According to species of the substrate, hydroxyl group, hydroxymethyl group, amino group and carboxyl group of the reaction component or the reaction product may be protected by the above protecting group before or after the isocyanation reaction. Introduction and elimination of these protecting groups may be carried out by a method similar to the above described method.

In the production process of adamantane derivatives mentioned above, a nitro group and a hydroxyl group can be introduced into an adamantane backbone in one step by, in the presence of the imide compound, allowing an adamantane compound having at least two methane carbon atoms in the adamantane backbone to react with a nitrogen oxide and oxygen to be used in the nitration reaction. A derivative in which at least two functional groups selected from a nitro group, a hydroxyl group and a carboxyl group are introduced to the adamantane backbone can be obtained in one step by allowing the adamantane compound to react with a nitrogen oxide, oxygen and carbon monoxide in the presence of the imide compound. The reaction may be carried out in accordance with the conditions and operations described in the paragraphs of the nitration reaction, the oxidation reaction or the carboxylation reaction depending on the objective compound.

For example, when adamantane is allowed to react with nitrogen monoxide, oxygen and carbon monoxide in the presence of the imide compound, 1-carboxy-3-nitro-5-adamantanol, 1-nitro-3,5-adamantanediol, 1-carboxy-3,5-adamantanediol, 1,3,5-adamantanetriol, 1,3-dinitro-5-adamantanol, 1,3-dicarboxy-5-adamantanol etc can be obtained.

As to the process for producing an adamantane derivative having a hydroxyl group and a functional group, as a preferred production process, there may be mentioned, for example, a process for oxidizing an adamantane derivative shown by the following formula (1a):

(Ia)

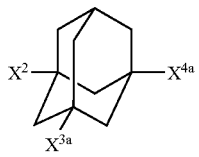

wherein $X^2$ represents a nitro group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group; $X^{3a}$ and $X^{4a}$ may be the same or different from each other and each may represent a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanto group; with oxygen in the presence of an oxidation catalyst comprising the imide compound shown by the formula (2) or the imide compound and a co-catalyst.

According to the more preferable process for producing the group derivative, in the above formula (1a), (i) when $X^2$ is a nitro group, $X^{3a}$ and $X^{4a}$ may be the same or different from each other and each may represent a hydrogen atom, an alkyl group, a nitro group;

(ii) when $X^2$ is an amino group or N-substituted amino group which may be protected by a protective group, $X^{3a}$ and $X^{4a}$ may be the same or different from each other and each may represent a hydrogen atom, an alkyl group, an amino group or N-substituted amino group which may be protected by a protective group;

(iii) when $X^2$ is a hydroxyl group which may be protected by a protective group, $X^3$ and $X^4$ may be the same or different from each other and each may represent a hydrogen atom, an alkyl group, a hydroxyl group which may be protected by a protective group;

(iv) when $X^2$ is a carbonyl group which may be protected by a protective group, $X^{3a}$ and $X^{4a}$ may be the same or different from each other and each may represent a hydrogen atom, an alkyl group, a carboxyl group which may be protected by a protective group;

(v) when X is a hydroxymethyl group which may be protected by a protective group, $X^3$ and $X^4$ may be the same or different from each other and each may represent a hydrogen atom, an alkyl group, a hydroxymethyl group which may be protected by a protective group; and (vi) when $X^2$ is an isocyanato group, $X^3$ and $X^4$ may be the same or different from each other and each may represent a hydrogen atom, an alkyl group or an isocyanato group.

In the production of the novel adamantane derivative, a conventional oxidation process such as an oxidation process using nitric acid or chromic acid, oxidation process using an cobalt salt as a catalyst, a biochemical method or the like may be employed as an oxidation process. For the introduction of a hydroxyl group, these may be employed a process for introducing a hydroxyl group to a substrate which comprises introducing a halogen atom (e.g., a bromine atom) to the substrate and then, hydrolyzing with the use of an inorganic salt such as silver nitrate and silver sulfate.

A compound having a basic group or an acidic group among adamantane derivatives having a hydroxyl group and a functional group may form its salt. For example, an adamantane derivative having a carboxyl group may form a salt by being reacted with a basic compound. As the basic compound, use can be made of, for example, besides ammonia, the compound (Ia) having an amino group and the compound (Id) having an amino group, and basic compounds (e.g., an organic base and an inorganic base) exemplified in the paragraphs of the reaction with a hydrocarbon halide.

Moreover, among adamantane derivatives having a hydroxyl group and a functional group, a compound having a basic group such as an adamantane derivative having an amino group may form a salt by being reacted with an acid. An acid includes, for example, an inorganic acid (e.g., hydrochloric acid, sulfuric acid, nitric acid, hydrochloric acid), an organic acid (e.g., an aliphatic carboxylic acid such as acetic acid and propionic acid; an aromatic carboxylic acid such as benzoic acid; an alkylsulfonic acid such as methanesulfonic acid, ethanesulfonic acid; an arylsulfonic acid such as benzenesulfonic acid, p-toluenesulfonic acid).

Reactions such as oxidation reaction may be effected in any of a batch system, a semi-batch system and a continuous system. After completion of the reaction, a reaction product can be easily isolated and purified according to a conventional means such as filtration, condensation, distillation, extraction, crystallization, recrystallization and column chromatography, or a combination of these means.

INDUSTRIAL APPLICABILITY

In the process of the present invention, an adamantane derivatives shown by the formula (2) or a known adamantane derivative can be efficiently produced with high conversion and selectivity.

Such adamantane derivatives are useful as raw materials for high functional materials (e.g., optical materials such as optical fibers, optical elements, optical lenses, hologram, optical discs and contact lenses; transparent resin coating compositions for organic glasses; electric conductive polymers; photosensitive materials; fluorescent materials). Moreover, the adamantane derivatives are also useful as raw materials of pharmaceutical preparations having high pharmacological activity and agricultural chemicals.

The present invention can provide a novel adamantane derivative which is useful as a high functional material. Moreover, the use of an oxidation catalyst comprising a specific imide compound can provide not only the novel compound but also known adamantane derivatives efficiently. Further, the adamantane derivatives can be obtained in high conversion and selectivity even under mild or moderate conditions.

EXAMPLES

The following examples are intended to describe the present invention in more detail, but should by no means be construed to limit the scope of the invention. Incidentally, infrared absorption spectra were measured after purifying the reaction product by column chromatography. The terms "Ac" and "Ph" represent acetyl group and phenyl group, respectively.

Example 1

Mixture of 10 mmole 1-acetylaminoadamantane (Aldrich chemical Company, Inc.), 1 mmole of N-hydroxyphthalimide (NHPI), 0.05 mmole of vanadium (III) acetylacetonato ($V(AA)_3$) and 25 mL of acetic acid was stirred under an oxygen atmosphere and the conditions represented in Table 1 (temperature and time). The products in the reaction mixture were analyzed by gas chromatography, and, as a result, 1-acetylamino-3-adamantanol (compound 1), 1-acetylamino-3,5-adamantanediol (compound 2) and 1-acetylamino-4-adamantanone (compound 3) were obtained with conversions and yields represented in Table 1.

TABLE 1

| Temperature (° C.) | Time (hr) | Conversion (%) | Yield (%) Comp.1 | Comp.2 | Comp.3 |
|---|---|---|---|---|---|
| 75 | 6 | 89 | 64 | 16 | 8 |
| 60 | 20 | 92 | 66 | 19 | 4 |

Comp.1 (compound 1): 1-acetylamino-3-adamantanol
Comp.2 (compound 2): 1-acetylamino-3,5-adamantanediol
Comp.3 (compound 3): 1-acetylamino-4-adamantanone

Example 2

A reactor was charged with 10 mmole of adamantane, 1 mmole of NHPI, 0.005 mmole of $Co(AA)_2$ and 25 mL of acetic acid, then equipped with a gas bag of mixed gas (a mixed gas of 2 L of carbon monoxide and 0.5 L of oxygen). The resultant mixture was stirred for 6 hours at a temperature of 60° C. to give 1-carboxyadamantane and 1,3-dicarboxyadamantane.

A mixture of 10 mmole of 1-carboxyadamantane, 1 mmole of NHPI, 0.05 mmole of $V(AA)_3$ and 25 mL of acetic acid was stirred under an oxygen atmosphere and the conditions represented in Table 2 (time and temperature). As a result, 1-carboxy-3-adamantanol (compound 1), 1-carboxy-3,5-adamantanediol (compound 2) and 1-carboxy-4-adamantanone (compound 3) were obtained with conversions and yields represented in Table 2.

TABLE 2

| Temperature (° C.) | Time (hr) | Conversion (%) | Yield (%) Comp.1 | Comp.2 | Comp.3 |
|---|---|---|---|---|---|
| 75 | 1 | 64 | 44 | 8 | 3 |
| 75 | 2 | 78 | 59 | 12 | 4 |
| 75 | 5 | 90 | 64 | 19 | 4 |
| 75 | 8 | 94 | 52 | 29 | 5 |

Comp.1 (compound 1): 1-carboxy-3-adamantanol
Comp.2 (compound 2): 1-carboxy-3,5-adamantanediol
Comp.3 (compound 3): 1-carboxy-4-adamantanone

Example 3

In the presence of an acid catalyst (p-toluenesulfonic acid), 1-carboxyadamantane obtained in Example 2 was allowed to react with an excess amount of ethanol to give 1-ethoxycarbonyladamantane.

A mixture of 10 mmole of the 1-ethoxycarboxyadamantane, 1 mmole of NHPI, 0.05 mmole of $V(AA)_3$ and 25 mL of acetic acid was stirred under an oxygen atmosphere and the conditions represented in Table 3 (temperature and time). As a result, 1-ethoxycarbonyl-3-adamantanol (compound 1), 1-ethoxycarbonyl-3,5-adamatanediol (compound 2) and 1-ethoxy-4-carbonyladamantanone (compound 3) were obtained with conversions and yields represented in Table 3.

TABLE 3

| Temperature (° C.) | Time (hr) | Conversion (%) | Yield (%) Comp.1 | Comp.2 | Comp.3 |
|---|---|---|---|---|---|
| 75 | 6 | 95 | 58 | 16 | 8 |
| 75 | 3 | 86 | 68 | 6 | 7 |

TABLE 3-continued

| Temperature (° C.) | Time (hr) | Conversion (%) | Yield (%) Comp.1 | Comp.2 | Comp.3 |
|---|---|---|---|---|---|
| 60 | 6 | 63 | 48 | 6 | 4 |
| 60 | 20 | 92 | 54 | 16 | 7 |
| 75 | 15 | 99 | 27 | 43 | 5 |

Comp.1 (compound 1): 1-ethoxycarbonyl-3-adamantanol
Comp.2 (compound 2): 1-ethoxycarbonyl-3,5-adamantanediol
Comp.3 (compound 3): 1-ethoxycarbonyl-4-adamantanone

Example 4

An eggplant type flask (50 mL) with side arm was dipped in iced water and the pressure was reduced. Into the flask, nitrogen monoxide was introduced from a gas bag (1 L) and further oxygen was introduced from a gas bag (1 L). The flask was filled with reddish-brown gas, and then a blue liquid comprising $N_2O_3$ as a main component was formed with sedimentation of the reddish-brown gas. The introductions of the nitrogen monoxide and oxygen were repeated to produce about 1.5 ml of the blue liquid. The blue liquid was frozen with the use of liquid nitrogen.

1.8 g (0.024 mole based on $N_2O_3$ basis) of the frozen blue liquid, 1 mmole of adamantane, 0.05 mmole of NHPI and 5 ml of acetic acid were mixed, and then the mixture was reacted for 10 hours at 100° C. with stirring to give 1-nitroadamantane and 1,3-dinitroadamantane.

To 25 mL of acetic acid was added 10 mmole of the 1-nitroadamantane, 1 mmole of NHPI and 0.05 mmole of $V(AA)_3$, and the resultant mixture was stirred for 8 hours at 75° C., under an oxygen atmosphere. The products in the reaction mixture were analyzed by gas chromatography, and, as a result, 1-nitro-3-adamantanol (yield 48%), 1-nitro-3,5-adamantanediol (yield 19%) and 1-nitro-3,5,7-adamantanetriol (yield 2%) were formed with conversion of 76% of 1-nitroadamantane. Moreover, these products were analyzed by mass spectroscopy.

(1) 1-nitro-3-adamantanol
Pale yellow solid
Mass spectral data (fragment)
$[M]^+$: 181,$[M]^-$: 163(—$OH_2$), $[M]^{--}$: 117(—$NO_2$)

(2) 1-nitro-3,5-adamantanediol
Pale yellow solid
Mass spectral data (fragment)
$[M]^+$: 197, $[M]^-$: 179(—$OH_2$), $[M]^{--}$: 133(—$NO_2$)

Example 5

A mixture of 10 mmole of 1,3-dinitroadamantane obtained in Example 4, 1 mmole of NHPI, 0.05 mmole of $V(AA)_3$ and 25 mL of acetic acid was mixed and stirred for 8 hours at 85° C., under an oxygen atmosphere. As a result, 1,3-dinitro-5-adamantanol (yield 46%) and 1,3-dinitro-5,7-adamantanediol (yield 24%) were formed. The conversion of 1,3-dinitroadamantane was 79%.

(1) 1,3-dinitro-5-adamantanol
Pale yellow solid
Mass spectral data (fragment)
$[M]^+$: 226, $[M]^-$: 208(—$OH_2$), $[M]^{--}$: 162(—$NO_2$), $[M]^{---}$: 115 (—$HNO_2$)

(2) 1,3-dinitro-5,7-adamantanediol
Pale yellow solid
Mass spectral data (fragment)
$[M]^+$: 242, $[M]^-$: 224(—$OH_2$), $[M]^{--}$: 178(—$NO_2$), $[M]^{---}$: 131 (—$HNO_2$)

Example 6

A mixture of 10 mmole of 1-carboxyadamantane obtained in Example 2, 1 mmole of NHPI, 0.05 mmole of $V(AA)_3$ and 25 mL of acetic acid was mixed and stirred for 8 hours at 75° C., under an oxygen atmosphere. As a result, 1-carboxy-3-adamantanol (yield 28%), 1-carboxy-3,5-adamantanediol (yield 48%) and 1-carboxy-3,5,7-adamantanetriol (yield 10%) were formed. The conversion of 1-carboxyadamantane was 94%.

(1) 1-carboxy-3-adamantanol
White solid
Mass spectral data (fragment)
$[M]^+$: 196, $[M]^-$: 178(—$OH_2$), $[M]^{--}$: 133(—COOH)

(2) 1-carboxy-3,5-adamantanediol
White solid
Mass spectral data (fragment)
$[M]^+$: 212, $[M]^-$: 194(—$OH_2$), $[M]^-$: 149(—COOH)

Example 7

A mixture of 10 mmole of 1,3-dicarboxyadamantane obtained in Example 2, 1 mmole of NHPI, 0.05 mmole of $V(AA)_3$ and 25 mL of acetic acid was mixed and stirred for 8 hours at 85° C., under an oxygen atmosphere. As a result, 1,3-dicarboxy-5-adamantanol (yield 52%) and 1,3-dicarboxy-5,7-adamantanediol (yield 26%) were formed. The conversion of 1,3-dicarboxyadamantane was 86%.

(1) 1,3-dicarboxy-5-adamantanol
White solid
Mass spectral data (fragment)
$[M]^+$: 228, $[M]^-$: 210(—$OH_2$), $[M]^{--}$: 165(—COOH), $[M]^{---}$: 119(—HCOOH)

(2) 1,3-dicarboxy-5,7-adamantanediol
White solid
Mass spectral data (fragment)
$[M]^+$: 244, $[M]^-$: 216(—$OH_2$), $[M]^{--}$: 171(—COOH), $[M]^{---}$: 125(—HCOOH)

Example 8

A mixture of 10 mmole of adamantane, 1 mmole of NHPI, 0.05 mmole of cobalt(II) acetylacetonato ($Co(AA)_2$) and 25 mL of acetic acid was stirred for 6 hours at 75° C. under an oxygen atmosphere to give 1-acetyloxyadamantane and 1,3-diacetyloxyadamantane.

To 25 mL of acetic acid were added 10 mmole of the 1-acetyloxyadamantane, 1 mmole of NHPI and 0.05 mmole of $V(AA)_2$, and the resultant mixture was stirred for 8 hours at 75° C., under an oxygen atmosphere. As a result, 1-acetyloxy-3-adamantanol (yield 37%), 1-acetyloxy-3,5-adamantanediol (yield 25%) and 1-acetyloxy-3,5,7-adamantanetriol (yield 11%) were formed. The conversion of 1-acetyloxyadamantane was 89%.

(1) 1-acetyloxy-3-adamantanol
White solid
Mass spectral data (fragment)
$[M]^+$: 210, $[M]^-$: 151(—OAc), $[M]^{--}$: 133(—$OH_2$)

(2) 1-acetyloxy-3,5-adamantanediol
White solid
Mass spectral data (fragment)
$[M]^+$: 226, $[M]^-$: 167(—OAc), $[M]^{--}$: 149(—$OH_2$)

Example 9

To 25 mL of acetic acid were added 10 mmole of 1,3-diacetyloxyadamantane obtained in Example 8, 1 mmole of NHPI and 0.05 mmole of $V(AA)_3$, and the resultant mixture was stirred for 8 hours at 85° C. under an oxygen atmosphere. As a result, 1,3-diacetyloxy-5-adamantanol (yield 60%) and 1,3-diacetyloxy-5,7-adamantanediol (yield 19%) were formed. The conversion of 1,3-diacetyloxyadamantane was 93%.

(1) 1,3-diacetyloxy-5-adamantanol
White solid
Mass spectral data (fragment)
$[M]^+$: 268, $[M]^-$: 209(—OAc), $[M]^{--}$: 191(—$OH_2$), $[M]^{---}$: 131 (—HOAc)

(2) 1,3-diacetyloxy-5,7-adamantanediol
White solid
Mass spectral data (fragment)
$[M]^+$: 284, $[M]^-$: 225(—OAc), $[M]^{--}$: 207(—$OH_2$), $[M]^{---}$: 147 (—HOAc)

Example 10

A mixture of 10 mmole of 1-benzoylaminoadamantane (Aldrich chemical company, Inc.), 1 mmole of NHPI, 0.05 mmole of $V(AA)_3$ and 25 mL of acetic acid was mixed and stirred for 8 hours at 75° C. under an oxygen atmosphere. As a result, 1-benzoylamino-3-adamantanol (yield 53%), 1-benzoylamino-3,5-adamantanediol (yield 23%) and 1-benzoylamino-3,5,7-adamantanetriol (yield 7%) were formed. The conversion of 1-benzoylaminoadamantane was 91%.

(1) 1-benzoylamino-3-adamantanol
Pale yellow solid
Mass spectral data (fragment)
$[M]^+$: 271, $[M]^-$: 253(—$OH_2$), $[M]^{--}$: 133(—NHCOPh)

(2) 1-benzoylamino-3,5-adamantanediol
Pale yellow solid
Mass spectral data (fragment)
$[M]^+$: 287, $[M]^-$: 269(—$OH_2$), $[M]^{--}$: 149(—NHCOPh)

Example 11

In the presence of an acid catalyst (p-toluenesulfonic acid), 1-carboxyadamantane obtained in Example 2 was allowed to react with an excess amount of methanol to give 1-methoxycarbonyladamantane.

A mixture of 10 mmole of the 1-methoxycarbonyladamantane, 1 mmole of NHPI, 0.05 mmole of $V(AA)_3$ and 25 mL of acetic acid was mixed and stirred for 8 hours at 75° C., under an oxygen atmosphere. As a result, 1-methoxycarbonyl-3-adamantanol (yield 47%), 1-methoxycarbonyl-3,5-adamantanediol (yield 31%) and 1-methoxycarbonyl-3,5,7-adamantanetriol (yield 8%) were formed. The conversion of 1-methoxycarbonyladamantane was 95%.

(1) 1-methoxycarbonyl-3-adamantanol
White solid
Mass spectral data (fragment)
$[M]^+$: 212, $[M]^-$: 194(—$OH_2$), $[M]^{--}$: 179(—$CH_3$), $[M]^{---}$: 135(—COO)

(2) 1-methoxycarbonyl-3,5-adamantanediol
White solid
Mass spectral data (fragment)
$[M]^+$: 228, $[M]^-$: 210(—$OH_2$), $[M]^{--}$: 195(—$CH_3$), $[M]^{---}$: 151 (—COO)

Example 12

In the presence of an acid catalyst (p-toluenesulfonic acid), 1,3-dicarboxyadamantane obtained in Example 2 was allowed to react with an excess amount of methanol to give 1,3-dimethoxycarbonyladamantane.

To 25 mL of acetic acid were added the 10 mmole of the 1,3-dimethoxycarbonyladamantane, 1 mmole of NHPI and 0.05 mmole of $V(AA)_3$, and the resultant mixture was stirred for 8 hours at 85° C., under an oxygen atmosphere. As a result, 1,3-dimethoxycarbonyl-5-adamantanol (yield 42%) and 1,3-methoxycarbonyl-5,7-adamantanediol (yield 36%) were formed. The conversion of 1,3-dimethoxycarbonyladamantane was 92%.

(1) 1,3-dimethoxycarbonyl-5-adamantanol

White solid

Mass spectral data (fragment) $[M]^+$: 272, $[M]^-$: 254(—$OH_2$), $[M]^{--}$: 239(—$CH_3$), $[M]^{---}$: 195(—COO)

(2) 1,3-dimethoxycarbonyl-5,7-adamantanediol

White solid

Mass spectral data (fragment)

$[M]^+$: 288, $[M]^-$: 270(—$OH_2$), $[M]^{--}$: 255(—$CH_3$), $[M]^{---}$: 211 (—COO)

Example 13

In an atmosphere of nitrogen, 10 mmole of 1-carboxy-3-adamantanol obtained by the method of Example 2 was dissolved in 10 ml of N,N-dimethylformamide (DMF). To the mixture, 15 mmole of tionyl chloride was added dropwise over 30 minutes while heating the mixture to the reflux temperature so as to begin to reflux at about the time the addition is finished. After refluxing for 2 hours, the mixture was cooled. To the mixture, 25 mmole of dimethylamine was added dropwise over 30 minutes while keeping the temperature of the solution at 10° C. or below, and the mixture was stirred for another 2 hours. As a result, the conversion of 1-carboxy-3-adamantanol was 99%, and 1-(N,N-dimethylcarbamoyl)-3-adamantanol (yield 95%) was formed.

Pale yellow solid

Mass spectral data $[M]^+$: 223

IR($cm^{-1}$): 3360, 1650, 700

Example 14

In an atmosphere of nitrogen, 10 mmole of 1-nitro-3-adamantanol obtained by the method of Example 4 and 12 mmole of triethylamine were dissolved in 10 ml of DMF. To the mixture, 11 mmole of acetyl chloride was added dropwise over 30 minutes at 40° C. The mixture was stirred for another 3 hours at 40° C. As a result, the conversion of 1-nitro-3-adamantanol was 99%, and 1-acetyloxy-3-nitroadamantane (yield 95%) was formed.

Pale yellow liquid

Mass spectral data $[M]^+$: 210

IR($cm^{-1}$): 1720, 1570, 1340

Example 15

An autoclave was charged, 10 mmole of 1-acetyloxy-3-nitroadamantane obtained by the method of Example 14, 5% Pd-C (10 mole % of Pd relative to a substrate), 1 ml of dilute hydrochloric acid and 10 ml of methanol. The mixture was stirred for 2 hours at 80° C. in an atmosphere of hydrogen at 30 atm. As a result, the conversion of 1-acetyloxy-3-nitroadamantane was 90%, and 1-acetyloxy-3-aminoadamantane (yield 70%) was formed.

Pale yellow liquid

Mass spectral data $[M]^+$: 209

IR($cm^{-1}$): 3310, 1650, 1620

Example 16

Operation was effected in the same manner as Example 15 except for using 1-nitro-3-adamantanol obtained by the method of Example 4 instead of 1-acetyloxy-3-nitroadamantane. 1-amino-3-adamantanol (yield 95%) was formed. The conversion of 1-nitro-3-adamantanol was 99%.

Pale yellow solid

Mass spectral data $[M]^+$: 167

IR($cm^{-1}$): 3370, 3340, 1620, 1360

In an atmosphere of nitrogen, 10 mmole of 1-amino-3-adamantanol obtained by the above method and 24 mmole of triethylamine were dissolved in 10 ml of DMF. To the mixture, 22 mmole of acetyl chloride was added dropwise over 30 minutes at 40° C. The mixture was stirred for another 3 hours at 40° C. As a result, the conversion of 1-amino-3-adamantanol was 90%, and 1-acetylamino-3-acetyloxyadamantane (yield 80%) was formed.

Pale yellow liquid

Mass spectral data $[M]^+$: 251

IR($cm^{-1}$): 3300, 1680, 1620

Incidentally, another operation was effected in the same manner as that of the above reaction except for using 1,3-adamantanediol instead of 1-amino-3-adamantanol. 1,3-bis(acetyloxy)adamantane (yield 95%) was obtained. The conversion of 1,3-adamantanediol was 99%.

Colorless liquid

Mass spectral data $[M]^+$: 252

IR($cm^{-1}$): 1630, 1210, 1020

Example 17

In an atmosphere of nitrogen, 10 mmole of 1-carboxy-3-adamantanol obtained by the method of Example 2 was dissolved in 10 ml of DMF. To the mixture, 15 mmole of tionyl chloride was added dropwise over 30 minutes while heating the mixture to the reflux temperature so as to begin to reflux at about the time the addition is finished. After refluxing for 2 hours, the mixture was cooled. To the mixture, 20 mmole of triethylamine was added and 11 mmole of methanol was added dropwise over 30 minutes while keeping the temperature of the solution at 10° C. or below, and the mixture was stirred for another 2 hours. As a result, the conversion of 1-carboxy-3-adamantanol was 99%, and 1-methoxycarbonyl-3-adamantanol (yield 95%) was formed.

White solid

Mass spectral data $[M]^+$: 210

IR($cm^{-1}$): 3350, 1730, 1130

Another operation was effected in the same manner as Example 14 except for using 1-methoxycarbonyl-3-adamantanol obtained by the method of Example 14 instead of 1-nitro-3-adamantanol. As a result, 1-acetyloxy-3-methoxycarbonyadamantane (yield 80%) was formed. The conversion of 1-methoxycarbonyl-3-adamantanol was 95%.

Colorless liquid

Mass spectral data $[M]^+$: 252

IR($cm^{-1}$): 1660, 1620, 1240

Example 18

In an atmosphere of nitrogen, 15 mmole of lithium aluminium hydride was suspended into 15 mL of tetrahydrofurane (THF). To the resultant mixture was slowly added 10 mmole of 1-carboxy-3-adamantanol obtained by the method of Example 2 while keeping the temperature of the mixture at 10° C. or below by using an ice bath. After warming the mixture to room temperature, the mixture was refluxed for 16 hours. As a result, 1-hydroxymethyl-3-adamantanol (yield 95%) was obtained. The conversion of 1-carboxy-3-adamantanol was 99%.

White solid

Mass spectral data $[M]^+$: 182

IR($cm^{-1}$): 3370, 1380, 1120

Another operation was effected in the same manner as Example 14 except for using 1-hydroxymethyl-3-adamantanol obtained by the above method instead of 1-nitro-3-adamantanol. 1-acetyloxy-3-hydroxymethyladamantane (yield 80%) was formed. The conversion of 1-hydroxymethyl-3-adamantanol was 90%.

Colorless liquid

Mass spectral data $[M]^+$: 224

IR($cm^{-1}$): 3310, 1640, 1230

Example 19

Another operation was effected in the same manner as Example 14 except for using 1-carboxy-3-adamantanol obtained by the method of Example 2 instead of 1-nitro-3-adamantanol. 1-acetyloxy-3-carboxyadamantane (yield 80%) was formed. The conversion of 1-carboxy-3-adamantanol was 90%.

Colorless liquid

Mass spectral data $[M]^+$: 238

IR($cm^{-1}$): 3000, 1640, 1600

In an atmosphere of nitrogen, 10 mmole of 1-acetyloxy-3-carboxyadamantane obtained by the above method was dissolved in 10 ml of DMF. To the mixture, 15 mmole of N,N'-carbodiimidazol in the form of powder was added in one portion. After stirring for 1 hour at the room temperature, 15 mmole of dimethylamine and 15 mmole of diazabicycloundecene were added. The mixture was heated to 100° C. and stirred for 8 hours. As a result, the conversion of 1-acetyloxy-3-carboxyadamantane was 80%, and 1-acetyloxy-3-(N,N-dimethylcarbamoyl)adamantane (yield 70%) was formed.

Pale yellow liquid

Mass spectral data $[M]^+$: 265

IR($cm^{-1}$): 1670, 1620, 1220

Example 20

In an atmosphere of nitrogen, 10 mmole of 1,3-adamantanediol and 12 mmole of pyridine was dissolved in 10 ml of DMF. To the mixture, 11 mmole of methoxycarbonyl chloride was added dropwise with stirring at room temperature. Cooling of the resultant mixture with ice was started at about the time exothermic reaction began. When the exothermic reaction is completed, the mixture was heated to 60° C. and then stirred for one hour. As a result, the conversion of 1,3-adamantanediol was 99% and 1-methoxycarbonyloxy-3-adamantanol (yield 85%) was formed.

Colorless liquid

Mass spectral data $[M]^+$: 226

IR($cm^{-1}$): 3320, 1620, 1240

Example 21

In an atmosphere of nitrogen, 10 mmole of 1,3-adamantanediol and 24 mmole of pyridine were dissolved in 10 ml of DMF. To the mixture, 22 mmole of methoxycarbonyl chloride was added dropwise with stirring at room temperature. Cooling of the resultant mixture with ice was started at about the time exothermic reaction began. When the exothermic reaction is completed, the mixture was heated to 60° C. and then stirred for one hour. As a result, the conversion of 1,3-adamantanediol was 99% and 1,3-bis(methoxycarbonyloxy)adamantane (yield 90%) was formed.

Colorless liquid

Mass spectral data $[M]^+$: 284

IR($cm^{-1}$): 1620, 1340, 1170

Example 22

In an atmosphere of nitrogen, 10 mmole of 1,3-adamantanediol and one drop of pyridine were dissolved in 10 ml of DMF. To the mixture, 10 mmole of methylisocyanato was added dropwise with stirring. Cooling of the resultant mixture with ice was started at about the time exothermic reaction began. When the exothermic reaction is completed, the mixture was heated to 60° C. and then stirred for one hour. As a result, the conversion of 1,3-adamantanediol was 99% and 1-(N-methylcarbamoyloxy)-3-adamantanol (yield 85%) was formed.

Pale yellow liquid

Mass spectral data $[M]^+$: 225

IR($cm^{-1}$): 3300, 1660, 1270

Example 23

In an atmosphere of nitrogen, 10 mmole of 1,3-adamantanediol and one drop of pyridine were dissolved in 10 ml of DMF. To the mixture, 20 mmole of methylisocyanato was added dropwise with stirring. Cooling of the resultant mixture with ice was started at about the time exothermic reaction began. When the exothermic reaction is completed, the mixture was heated to 60° C. and then stirred for one hour. As a result, the conversion of 1,3-adamantanediol was 99% and 1-(N-methylcarbamoyloxy)-3-adamantanol (yield 90%) was formed.

Pale yellow liquid

Mass spectral data $[M]^+$: 282

IR($cm^{-1}$): 1670, 1260, 1140

Example 24

Operation was effected in the same manner as Example 20 except for using 1-nitro-3-adamantanol obtained by the method of Example 4 instead of 1,3-adamantanediol. The conversion of 1-nitro-3-adamantanol was 99% and 1-methoxycarbonyloxy-3-nitroadamantane (yield 90%) was obtained.

Pale yellow liquid

Mass spectral data $[M]^+$: 255

IR($cm^{-1}$): 1620, 1560, 1340, 1170

Example 25

Operation was effected in the same manner as Example 20 except for using 1-caboxy-3-adamantanol obtained by the method of Example 5 instead of 1,3-adamantanediol. The conversion of 1-carboxy-3-adamantanol was 99% and 1-carboxy-3-methoxycarbonyloxyadamantane (yield 90%) was obtained.

White solid

Mass spectral data $[M]^+$: 254

IR($cm^{-1}$): 3030, 1670, 1620, 1430

Example 26

Operation was effected in the same manner as Example 20 except for using 1-methoxycarbonyl-3-adamantanol obtained by the method of Example 11 instead of 1,3-adamantanediol. The conversion of 1-methoxycarbonyl-3-adamantanol was 99% and 1-methoxycarbonyloxy-3-methoxycarbonyloxyadamantane (yield 90%) was obtained.

White solid

Mass spectral data $[M]^+$: 268

IR($cm^{-1}$): 1650, 1620, 1440, 1240

Example 27

Operation was effected in the same manner as Example 1 except for using 1-adamantanol instead of 1-acetylaminoadamantane and reacting for 6 hours at 75° C. The conversion of 1-adamantanol was 99% and 1-3-adamantanol (yield 80%) was obtained.

White solid

Mass spectral data $[M]^+$: 168

IR($cm^{-1}$): 3350, 1370, 1110

Another operation was effected in the same manner as Example 14 except for using 1,3-adamantanediol obtained by the above method instead of 1-nitro-3-adamantanol. The conversion of 1,3-admantanediol was 99% and 1-acetyloxy-3-adamantanol (yield 95%) was obtained.

Colorless liquid

Mass spectral data $[M]^+$: 210

IR($cm^{-1}$): 3350, 1720, 1120

Another operation was effected in the same manner as Example 20 except for using 1-acetyloxy-3-adamantanol obtained by the above method instead of 1,3-adamantanediol. The conversion of 1-acetyloxy-3-adamantanol was 99% and 1-acetyloxy-3-methoxycarbonyloxyadamantane (yield 90%) was obtained.

White solid

Mass spectral data $[M]^+$: 268

IR($cm^{-1}$): 1670, 1630, 1440, 1240

Example 28

In an atmosphere of nitrogen, 11 mmole of acetyl chloride and 12 mmole of triethylamine were dissolved in 2 mL of THF. To the resultant mixture, 10 mmole of a solution of 1-amino-3-adamantanol in DMF (10 mL) was added dropwise over 30 minutes at 40° C. The mixture was stirred for another 3 hours at 40° C. As a result, the conversion of 1-amino-3-adamantanol was 99%, and 1-acetylamino-3-adamantanol was 99%, and 1-acetylamino-3-adamantanol (yield 95%) was formed.

Pale yellow liquid

Mass spectral data $[M]^+$: 209

IR($cm^{-1}$): 3350, 1670, 690

Another operation was effected in the same manner as Example 20 except for using 1-acetylamino-3-adamantanol obtained by the above method instead of 1,3-adamantanediol. The conversion of 1-acetylamino-3-adamantanol was 99% and 1-acetylamino-3-methoxycarbonyloxyadamantane (yield 90%) was obtained.

Pale yellow liquid

Mass spectral data $[M]^+$: 267

IR($cm^{-1}$): 3300, 1650, 1620, 1240

Example 29

Operation was effected in the same manner as Example 20 except for using 1-hydroxymethyl-3-adamantanol obtained by the method of Example 18 instead of 1,3-adamantanediol. The conversion of 1-hydroxymethyl-3-adamantanol was 99% and 1-hydroxymethyl-3-methoxycarbonyloxyadamantane (yield 90%) was obtained.

White solid

Mass spectral data $[M]^+$: 240

IR($cm^{-1}$): 3300, 1650, 1440, 1240

Example 30

Operation was effected in the same manner as Example 20 except for using 1-(N,N-dimethylcarbamoyl)-3-adamantanol obtained by the method of Example 13 instead of 1,3-adamantanediol. The conversion of 1-(N,N-dimethylcarbamoyl)-3-adamantanol was 99% and 1-(N,N-dimethylcarbamoyl)-3-methoxycarbonyloxyadamantane (yield 90%) was obtained.

Pale yellow liquid

Mass spectral data $[M]^+$: 281

IR($cm^{-1}$): 1650, 1620, 1280, 1170

Example 31

In toluene (100 mL) was dissolved 10 mmole of 1-acetyloxy-3-aminoadamantane obtained by the method of Example 15. To the resultant solution was added 12 mmole of phosgene at room temperature and the mixture was stirred for 6 hours. As a result, the conversion of 1-acetyloxy-3-aminoadamantane was 95% and 1-acetyloxy-3-isocyanatoadamantane (yield 85%) was obtained.

Pale yellow liquid

Mass spectral data $[M]^+$: 235

IR($cm^{-1}$): 2200, 1670, 1330, 750

Example 32

Operation was effected in the same manner as Example 1 except for using 1,3-adamantanediol instead of 1-acetylaminoadamantane and reacting for 6 hours at 75° C. The conversion of 1,3-adamantanediol was 99% and 1,3,5-adamantanetriol (yield 80%) was obtained.

White solid

Mass spectral data $[M]^+$: 184

IR($cm^{-1}$): 3320, 1320, 1170

Another operation was effected in the same manner as Example 14 except for using 1,3,5-adamantanetriol obtained by the above method instead of 1-nitro-3-adamantanol. The conversion of 1,3,5-adamantanetriol was 99% and 1-acetyloxy-3,5-adamantanediol (yield 90%) was obtained.

Colorless liquid

Mass spectral data $[M]^+$: 226

IR($cm^{-1}$): 3320, 1620, 1320, 1140

Example 33

In an atmosphere of nitrogen, 10 mmole of 1,3,5-adamantanetriol obtained by the method of Example 32 and 24 mmole of triethylamine were dissolved in 10 mL of DMF. To the mixture, 22 mmole of acetylchloride was added dropwise over 30 minutes at 40° C. The mixture was stirred for another 3 hours at 40° C. As a result, the conversion of 1,3,5-adamantanetriol was 99%, and 1,3-bis(acetyloxy)-5-adamantanol (yield 80%) was formed.

Colorless liquid

Mass spectral data $[M]^+$: 268

IR($cm^{-1}$): 3300, 1610, 1310, 1150

Example 34

In an atmosphere of nitrogen, 10 mmole of 1,3,5-adamantanetriol obtained by the method of Example 32 and 36 mmole of triethylamine were dissolved in 10 mL of DMF. To the mixture, 33 mmole of acetyl chloride was added dropwise over 30 minutes at 40° C. The mixture was stirred for another 3 hours at 40° C. As a result, the conversion of 1,3,5-adamantanetriol was 99%, and 1,3,5-tris(acetyloxy) adamantane (yield 95%) was formed.

Colorless liquid

Mass spectral data $[M]^+$: 310

IR($cm^{-1}$): 1620, 1320, 1140

Example 35

Operation was effected in the same manner as Example 20 except for using 1,3,5-adamantanetriol obtained by the method of Example 32 instead of 1,3-adamantanediol. The conversion of 1,3,5-adamantanetriol was 99% and 1-methoxycarbonyloxy-3,5-adamantanediol (yield 90%) was formed.

Colorless liquid

Mass spectral data $[M]^+$: 242

IR($cm^{-1}$): 3320, 1620, 1270

Example 36

Operation was effected in the same manner as Example 21 except for using 1,3,5-adamantanetriol obtained by the method of Example 32 instead of 1,3-adamantanediol. The conversion of 1,3,5-adamantanetriol was 99% and 1,3-bis (methoxycarbonyloxy)-5-adamantanol (yield 80%) was obtained.

Colorless liquid

Mass spectral data $[M]^+$: 300

IR($cm^{-1}$): 3330, 1610, 1260

Example 37

In an atmosphere of nitrogen, 10 mmole of 1,3,5-adamantanetriol obtained by the method of Example 32 and 36 mmole of pyridine were dissolved in 10 mL of DMF. To the mixture, 33 mmole of methoxycarbonyl chloride was added dropwise with stirring at room temperature. Cooling of the resultant mixture with ice was started at about the time exothermic reaction began. When the exothermic reaction is completed, the mixture was heated to 60° C. and then stirred for one hour. As a result, the conversion of 1,3,5-adamantanetriol was 99% and 1,3,5-tris (methoxycarbonyloxy)adamantane (yield 95%) was formed.

Colorless liquid

Mass spectral data $[M]^+$: 358

IR($cm^{-1}$): 1630, 1280, 1110

Example 38

Operation was effected in the same manner as Example 22 except for using 1,3,5-adamantanetriol obtained by the method of Example 32 instead of 1,3-adamantanediol. The conversion of 1,3,5-adamantanetriol was 99% and 1-(N-methylcarbamoyloxy)-3,5-adamantanediol (yield 90%) was obtained.

Pale yellow liquid

Mass spectral data $[M]^+$: 241

IR($cm^{-1}$): 3350, 1670, 1280

Example 39

Operation was effected in the same manner as Example 23 except for using 1,3,5-adamantanetriol obtained by the method of Example 32 instead of 1,3-adamantanediol. The conversion of 1,3,5-adamantanetriol was 99% and 1,3-bis (N-methylcarbamoyloxy)-5-adamantanol (yield 80%) was obtained.

Pale yellow liquid

Mass spectral data $[M]^+$: 298

IR($cm^{-1}$): 3340, 1680, 1310

Example 40

In an atmosphere of nitrogen, 10 mmole of 1,3,5-adamantanetriol obtained by the method of Example 32 and one drop of pyridine were dissolved in 10 mL of DMF. To the mixture, 30 mmole of methylisocyanato was added dropwise with stirring. Cooling of the resultant mixture with ice was started at about the time exothermic reaction began. When the exothermic reaction is completed, the mixture was heated to 60° C. and then stirred for one hour. As a result, the conversion of 1,3,5-adamantanetriol was 99% and 1,3,5-tris(methylcarbamoyloxy)adamantane (yield 95%) was obtained.

Pale yellow liquid

Mass spectral data $[M]^+$: 339

IR($cm^{-1}$): 1670, 1310, 1140

Example 41

An eggplant type flask (50 mL) with side arm was dipped in iced water and its pressure was reduced. Into the flask, nitrogen monoxide was introduced from a gas bag (1 L) and further oxygen was introduced from a gas bag (1 L). The flask was filled with reddish-brown gas, and then a blue liquid comprising $N_2O_3$ as a main component was formed with sedimentation of the reddish-brown gas. The introductions of the nitrogen monoxide and oxygen were repeated to produce about 1.5 ml of the blue liquid. The blue liquid was frozen with the use of liquid nitrogen. 1.8g (0.024 mole based on $N_2O_3$ basis) of the frozen blue liquid, 1 mmole of 1,3-adamantanediol obtained by the method of Example 27, 0.05 mmole of NHPI and 5 mL of acetic acid were mixed, and then the mixture was reacted for 10 hours at a temperature of 100° C. with stirring to give 1-nitro-3,5-adamantanediol (yield 80%). The conversion of 1,3-adamantanediol was 99%.

Pale yellow liquid

Mass spectral data $[M]^+$: 213

IR($cm^{-1}$): 3320, 1320, 1170

Example 42

Operation was effected in the same manner as Example 21 except for using 1-nitro-3,5-adamantanediol obtained by the method of Example 41 instead of 1,3-adamantanediol. The conversion of 1-nitro-3,5-adamantanediol was 99% and 1,3-bis(methoxycarbonyloxy)-5-nitroadamantane (yield 90%).

Pale yellow liquid

Mass spectral data $[M]^+$: 349

IR($cm^{-1}$): 1650, 1590, 1360, 1120

Example 43

A reactor was charged with 10 mmole of 1,3-adamantanediol, 1 mmole of NHPI, 0.005 mmole of $Co(AA)_2$ and 25 mL of acetic acid, then equipped with a gas bag of mixed gas (a mixed gas of 2 L of carbon monoxide and 0.5 L of oxygen; pressure: 5 kg/cm). The resultant mixture was stirred for 6 hours at 60° C. to give 1-carboxy-3,5-adamantanediol (yield 80%). The conversion of 1,3-adamantanediol was 99%.

White solid

Mass spectral data $[M]^+$: 212

IR($cm^{-1}$): 3320, 1320, 1170

Operation was effected in the same manner as Example 21 except for using 1-carboxy-3,5-adamantanediol obtained by the above method instead of 1,3-adamantanediol. The conversion of 1-carboxy-3,5-adamantanediol was 99% and 1-carboxy-3,5-bis(methoxycarbonyloxy)adamantane (yield 90%).

Colorless liquid

Mass spectral data $[M]^+$: 240

IR($cm^{-1}$): 3370, 1670, 1470, 1320

Example 44

The mixture of 10 mmole of 1-carboxyadamantane, 1 mmole of NHPI, 0.005 mmole of $Co(AA)_2$ and 25 mL of acetic acid was stirred for 4 hours at 80° C. with introducing carbon monoxide and oxygen at a ratio of the former:the latter (molar ratio)=5:1 to give 1-carboxy-3-nitroadamantane in a 70% yield.

In an atmosphere of oxygen, the mixture of 10 mmole of 1-carboxy-3-nitroadamantane, 1 mmole of NHPI, 0.05 mmole of $V(AA)_3$ and 25 mL of acetic acid was allowed to react for 4 hours at 85° C. The reaction products were analyzed by gas-mass spectroscopy, and as a result, 1-carboxy-3-nitro-5-adamantanol was formed in a 80% yield.

Example 45

To a mixture of 10 mmole of adamantane, 1 mmole of NHPI, 0.005 mmole of $Co(AA)_2$ and 25 mL of acetic acid, nitrogen monoxide (NO), carbon monoxide (CO) and oxygen ($O_2$) were introduced at a ratio of NO:CO:$O_2$ (molar ratio)=10:15:1 (pressure: 26 kg/$cm^2$). The mixture was stirred for 6 hours at 100° C. The reaction products were analyzed by gas-mass spectroscopy, and as a result, the conversion of adamantane was 90%, and 1-carboxy-3-nitro-5-adamantanol (yield 5%), 1-nitro-3,5-adamantanediol (yield 10%), 1-carboxy-3,5-adamantanediol (yield 10%), 1,3,5-adamantanetriol (yield 15%), 1,3-dinitro-5-adamantanol (yield 8%), 1,3-dicarboxy-5-adamantanol (yield 3%), 1,3,5-trinitroadamantane (yield 5%), 1-carboxy-3,5-dinitroadamantane (yield 5%), 1,3-dicarboxy-5-nitroadamantane (yield 1%) and 1,3,5-tricarboxyadamantane (yield 1%) were formed.

Example 46

A reactor was charged with 10 mmole of adamantane, 1 mmole of NHPI, 0.005 mmole of $Co(AA)_2$ and 25 mL of acetic acid, then equipped with a gas bag of a mixed gas (a mixed gas of 3 L of carbon monoxide and 0.75 L of oxygen). The resultant mixture was stirred for 12 hours at 60° C. to give 1,3,5-tricarboxyadamantane together with 1-carboxyadamantane and 1,3-dicarboxyadamantane.

In an atmosphere of oxygen, to 25 mL of acetic acid was added 10 mmole of the 1,3,5-tricarboxyadamantane, 1 mmole of NHPI and 0.005 mmole of $Co(AA)_2$ and the mixture was stirred for 6 hours at 75° C. As a result, the conversion was 76% and 1,3,5-tricarboxy-7-adamantanol was obtained in a 70% yield.

(1) 1,3,5-tricarboxyadamantane

White solid

Mass spectral data (fragment)

$[M]^+$: 268, $[M]^{--}$: 223(—$CO_2H$), $[M]^{--}$: 178(—$CO_2H$), $[M]^{--}$: 133 (—$CO_2H$)

(2) 1,3,5-tricarboxy-7-adamantanol

White solid

Mass spectral data (fragment)

$[M]^+$: 284, $[M]^-$: 266(—$OH_2$), $[M]^{--}$: 221(—$CO_2H$), $[M]^{---}$: 176 (—$CO_2H$), $[M]^{----}$: 131 (—$CO_2H$)

What is claimed is:

1. An adamantane derivative shown by the following formula (1):

(1)

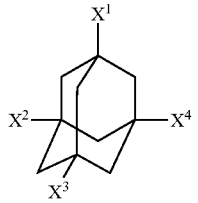

wherein $X^1$ represents a hydroxyl group which may be protected by a protective group, $X^2$ represents nitro group, an amino group or N-substituted amino group which may be protected by a protective group, a hydroxyl group which may be protected by a protective group, a carboxyl group which may be protected by a protective group, a hydroxymethyl group which may be protected by a protective group, or isocyanato group;

(i) when $X^2$ is nitro group, $X^3$ and $X^4$ are the same or different from each other and each represents a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanato group, excluding the case where $X^3$ and $X^4$ are both hydrogen atoms when $X^1$ is hydroxyl group and excluding 1,3,5-trinitro-7-adamantanol;

(ii) when $X^2$ is an amino group or N-substituted amino group which may be protected by a protective group, *$X^1$ is a hydroxyl group,* $X^3$ and $X^4$ are the same or different from each other and each represents a hydrogen atom, an alkyl group, an amino group or N-substituted amino group which may be protected by a protective group, a hydroxyl group which may be protected by a protective group, a carboxyl group which may be protected by a protective group, a hydroxymethyl group which may be protected by a protective group, or an isocyanato group, excluding the case where $X^3$ and $X^4$ are both hydrogen atoms or alkyl groups [when $X^1$ is hydroxyl group];

(iii) when $X^2$ is a hydroxyl group which may be protected by a protective group, $X^3$ and $X^4$ are the same or different from each other and each represents a hydrogen atom, an alkyl group, a hydroxyl group which may be protected by a protective group, a carboxyl group which may be protected by a protective group, a hydroxymethyl group which may be protected by a protective group, or an isocyanato group, excluding the case where $X^3$ and $X^4$ are both hydrogen atoms or alkyl groups when $X^1$ is hydroxyl group or a saturated aliphatic acyloxy group and $X^2$ is hydroxyl group or a saturated aliphatic acyloxy group and the case where $X^3$ and $X^4$ are a combination of hydrogen atom and a carboxyl group which may be protected by a protective group when $X^1$ and $X^2$ are both hydroxyl groups and excluding the case where each of $X^1$, $X^2$, $X^3$, and $X^4$ are all a hydroxyl group, or all a hydroxyl group protected by an acetyl group;

(iv) when $X^2$ is a carboxyl group which may be protected by a protective group, $X^3$ and $X^4$ are the same or different from each other and each represents a hydrogen atom, an alkyl group, a carboxyl group which may be protected by a protective group, a hydroxymethyl group which may be protected by a protective group, or an isocyanato group, excluding the case where $X^3$ and $X^4$ are both hydrogen atoms or alkyl groups or a combination of a hydrogen atom and an alkyl group when $X^1$ is a hydroxyl group or a saturated aliphatic acyloxy group;

(v) when $X^2$ is a hydroxymethyl group which may be protected by a protective group, $X^3$ and $X^4$ are the same or different from each other and each represents a hydrogen atom, an alkyl group, a hydroxymethyl group which may be protected by a protective group, or an isocyanato group, excluding the case where, $X^3$ and $X^4$ are both hydrogen atoms when $X^1$ is hydroxyl group; and (vi) when $X^2$ is isocyanato group, $X^3$ and $X^4$ are the same or different from each other and each represents a hydrogen atom, an alkyl group or an isocyanato group, excluding the case where, $X^3$ and $X^4$ are both hydrogen atoms when $X^1$ is hydroxyl group; or a salt thereof.

2. An adamantane derivative or a salt thereof according to claim w, wherein $X^1$ is hydroxyl group, a saturated $C_{2-6}$aliphatic acyloxy group, a $C_{1-6}$-alkoxy-carbonyloxy group or a carbamoyloxy group which may have a substituent and $X^2$ is nitro group, amino group, a $C_{2-6}$acylamino group, a $C_{1-6}$alkoxy-carbonylamino group, a saturated $C_{2-6}$aliphatic acyloxy group, a $C_{1-6}$alkoxy-carbonyloxy group, a carbamoyloxy group which may have a substituent, carboxyl group, a $C_{1-6}$alkoxy-carbonyl group, a carbamoyl group which may have a substituent, hydroxymethyl group or isocyanato group, in the formula (1).

3. A process for producing an adamantane derivative according to claim 1, which comprises, in the presence of an oxidation catalyst comprising an imide compound shown by the following formula (2):

(2)

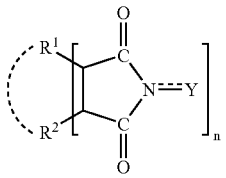

wherein $R^1$ and $R^2$ are the same or different from each other and each represents a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond or an aromatic or non-aromatic ring; Y represents oxygen atom or hydroxyl group; and n denotes an integer of 1 to 3; contacting an adamantane derivative shown by the (Ia)

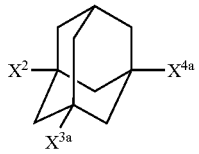

wherein $X^2$ represents an amino group or N-substituted amino group which may be protected by a protective group, a hydroxyl group which may be protected by a protective group, a carboxyl group which may be protected by a protective group, a hydroxymethyl group which may be protected by a protective group, or isocyanato group; $X^{3a}$ and $X^{4a}$ are the same or different from each other and each represents a hydrogen atom, an alkyl group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanato group; with oxygen.

4. A process according to claim 3, in the imide compound shown by the formula (2) $R^1$ and $R^2$ bond together to form a cycloalkane ring which may have a substituent, a cycloalkene ring which may have a substituent, a bridged hydrocarbon ring which may have a substituent or an aromatic ring which may have a substituent.

5. A process according to claim 3, wherein the imide compound shown by the formula (2) is a compound shown by the following formulae (2a) to (2f):

(2a)

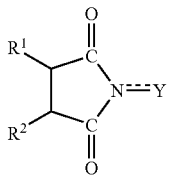

(2b)

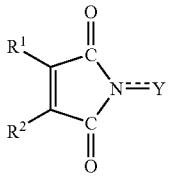

(2c)

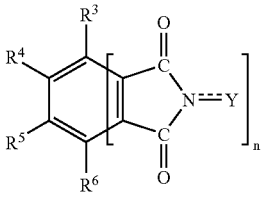

(2d)

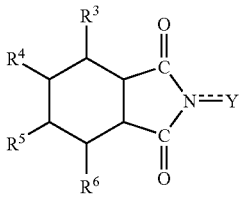

-continued (2e)

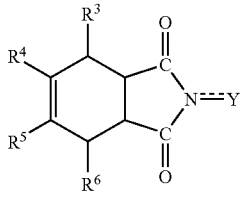

(2f)

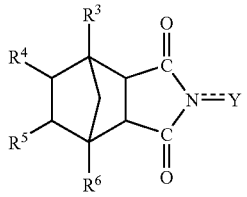

wherein $R^3$ to $R^6$ are the same or different from each other, and each represents a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$, Y and n have the same meanings as defined above.

6. A process according to claim 3, wherein the imide compound shown by the formula (2) is at least one compound selected from the group consisting of N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide and N,N'-dihydroxynaphthalenetetracarboximide.

7. A process according to claim 3, wherein said oxidation catalyst comprises the imide compound shown by the formula (2) and a co-catalyst.

8. A process according to claim 7, wherein said co-catalyst is a compound containing at least one element selected from the group consisting of a Group 2A element of the Periodic Table, a transition metal element and a Group 3B element of the Periodic Table.

9. A process according to claim 7, wherein said co-catalyst is a compound containing at least one element selected from the group consisting of a Group 3A element, a Group 4A element, a Group 5A element, a Group 6A element, a Group 7A element, a Group 8 element and a Group 1B element of the Periodic Table.

10. A process for producing an adamantane derivative according to claim 1, wherein the adamantane derivative has at least a hydroxyl group which comprises subjecting an adamantane derivative shown by the following formula (1a):

(Ia)

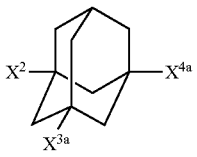

wherein $X^2$ represents nitro group, an amino group or N-substituted amino group which may be protected by a protective group, a hydroxyl group which may be protected by a protective group, a carboxyl group which may be protected by a protective group, a hydroxymethyl group which may be protected by a protective group, or isocyanato group; $X^{3a}$ and $X^{4a}$ are the same or different from each other and each represents a hydrogen atom, an alkyl group, a nitro group, a hydroxyl group which may be protected by a protective group, an amino group or N-substituted amino group which may be protected by a protective group, a carboxyl group which may be protected by a protective group, a hydroxymethyl group which may be protected by a protective group, or an isocyanato group;

to at least one step selected from the following oxidation step (i), nitration step (ii) and carboxylation step (iii):

(i) an oxidation step by oxygen in the presence of a catalyst comprising an imide compound shown by the following formula (2):

(2)

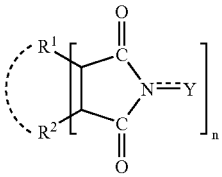

wherein $R^1$ and $R^2$ are the same or different from each other and each represents a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond or an aromatic or non-aromatic ring; Y represents oxygen atom or hydroxyl group; and n denotes an integer of 1 to 3 provided that in the oxidation step each of $X^2$, $X^{3a}$ and $X^{4a}$ in the formula (1a) is not nitro group;

(ii) at least one nitration step of the following (iia) and (iib):

(iia) a nitration step by a nitrogen oxide in the presence of a catalyst comprising the imide compound shown by the formula (2); and (iib) a nitration step by oxygen and at least one nitrogen oxide selected from dinitrogen oxide and nitrogen monoxide; and (iii) a carboxylation step by carbon monoxide and oxygen in the presence of a catalyst comprising the imide compound shown by the formula (2).

11. A process according to claim 10, which comprises further subjecting a reaction product to a reduction step after being subjected to at least one step selected from said nitration step (ii) and said carboxylation step (iii) to form at least one group selected from an amino group and a hydroxymethyl group.

*12. The compound 1,3,5-tricarboxyadamantane.*

*13. A composition comprising the compound 1,3,5-tricarboxyadamantane.*

* * * * *

UNITED STATES PATENT AND TRADEMARK OFFICE

CERTIFICATE OF CORRECTION

PATENT NO. : RE 39,744 E
APPLICATION NO. : 10/830494
DATED : July 24, 2007
INVENTOR(S) : Ishii et al.

It is certified that error appears in the above-identified patent and that said Letters Patent is hereby corrected as shown below:

Column 51, line 35, please correct the following:

"claim w, wherein $X^1$ is hydroxyl group, a saturated" should be --claim 1, wherein $X^1$ is hydroxyl group, a saturated--

Column 51, line 67 (last line), please correct the following:

"to 3; contacting an adamantane derivative shown by the" should be --to 3; contacting an adamantane derivative shown by the following formula (1a):--

Column 52, line 3, the label of the chemical formula at the top of column 52 should be corrected as follows:

"(Ia)" should be --(1a)--

Column 52, lines 51-58, the left bracket of formula (2c) should be displaced to the right as follows:

" (2c) "

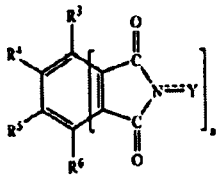

should be (2c)

-- 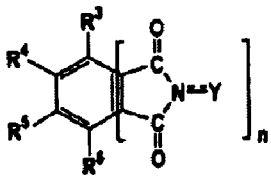 --

UNITED STATES PATENT AND TRADEMARK OFFICE

CERTIFICATE OF CORRECTION

PATENT NO. : RE 39,744 E
APPLICATION NO. : 10/830494
DATED : July 24, 2007
INVENTOR(S) : Ishii et al.

It is certified that error appears in the above-identified patent and that said Letters Patent is hereby corrected as shown below:

Column 53, line 56, the label of the chemical formula (Ia) should read corrected as follows:

"(Ia)" should be --(1a)--

Signed and Sealed this

Eighth Day of April, 2008

JON W. DUDAS
*Director of the United States Patent and Trademark Office*